(12) United States Patent
Mandelis et al.

(10) Patent No.: US 9,584,771 B2
(45) Date of Patent: Feb. 28, 2017

(54) SYSTEMS AND METHODS FOR THERMOPHOTONIC DYNAMIC IMAGING

(76) Inventors: Andreas Mandelis, Scarborough (CA); Nima Tabatabaei, Toronto (CA); Stephen Abrams, Toronto (CA)

( * ) Notice: Subject to any disclaimer, the term of this patent is extended or adjusted under 35 U.S.C. 154(b) by 524 days.

(21) Appl. No.: 13/522,936

(22) PCT Filed: Jan. 20, 2012

(86) PCT No.: PCT/CA2012/050035
§ 371 (c)(1),
(2), (4) Date: Dec. 16, 2013

(87) PCT Pub. No.: WO2012/135952
PCT Pub. Date: Oct. 11, 2012

(65) Prior Publication Data
US 2014/0085449 A1  Mar. 27, 2014

Related U.S. Application Data

(60) Provisional application No. 61/471,772, filed on Apr. 5, 2011.

(51) Int. Cl.
*G01N 21/71* (2006.01)
*H04N 7/18* (2006.01)
*A61B 5/00* (2006.01)

(52) U.S. Cl.
CPC ............ *H04N 7/183* (2013.01); *A61B 5/0073* (2013.01); *A61B 5/0088* (2013.01); *G01N 21/71* (2013.01)

(58) Field of Classification Search
CPC ..... A61B 5/0073; A61B 5/0088; G01N 21/71; H04N 7/183

(Continued)

(56) References Cited

U.S. PATENT DOCUMENTS 6,201,880 B1 * 3/2001 Elbaum ................. A61B 1/24
348/66
6,777,684 B1 * 8/2004 Volkov ............... G01N 21/3581
250/341.1

(Continued)

FOREIGN PATENT DOCUMENTS

EP      1258136     11/2002
WO    01/41421     6/2001

(Continued)

OTHER PUBLICATIONS

Breitenstein et al., "Lock-in Thermography", Springer Series in Advanced Microelectronics 10, Second Edition, Sep. 5, 2010.*

(Continued)

*Primary Examiner* — Jamie Atala
*Assistant Examiner* — James Boylan
(74) *Attorney, Agent, or Firm* — Lynn C. Schumacher; Stephen W. Leonard; Hill & Schumacher

(57) ABSTRACT

Systems and methods for improved thermophotonic imaging are provided in which both amplitude and phase image information is obtained with a high signal to noise ratio and depth-resolved capabilities. Image data obtained from an imaging camera is dynamically averaged and subsequently processed to extract amplitude and/or phase image data. The system may be configured for a wide range of imaging modalities, including single frequency modulation (thermophotonic lock-in imaging), Thermal-Wave Radar imaging or Thermophotonic Radar imaging involving chirp modulation, and Binary Phase Coded Modulation. Such imaging modalities may find application in many diverse areas, including non-destructive testing and biomedical diagnostic imaging including the imaging of teeth and monitoring changes in the tooth over time which are due to pathology such as dental caries or erosion.

47 Claims, 14 Drawing Sheets

(58) Field of Classification Search
USPC .......................................................... 348/77
See application file for complete search history.

(56) References Cited

U.S. PATENT DOCUMENTS

| | | | | |
|---|---|---|---|---|
| 7,551,769 | B2 | 6/2009 | Enachescu et al. | |
| 2004/0166471 | A1* | 8/2004 | Schussler | A61C 13/0004 433/72 |
| 2005/0056786 | A1* | 3/2005 | Shepard | G01N 25/72 250/341.4 |
| 2005/0283058 | A1* | 12/2005 | Choo-Smith | A61B 5/0088 600/315 |
| 2006/0063135 | A1* | 3/2006 | Mehl | A61C 13/0004 433/223 |
| 2007/0036420 | A1* | 2/2007 | Enachescu | G06T 7/001 382/141 |
| 2007/0138284 | A1* | 6/2007 | Giordano | H04N 1/02865 235/454 |
| 2010/0033730 | A1* | 2/2010 | Kim | G01B 9/02004 356/479 |
| 2010/0124731 | A1* | 5/2010 | Groscurth | A61C 9/00 433/213 |
| 2012/0070047 | A1* | 3/2012 | Johnson | G06T 11/001 382/128 |
| 2012/0146566 | A1* | 6/2012 | Takeuchi | G06F 1/025 318/503 |

FOREIGN PATENT DOCUMENTS

| | | |
|---|---|---|
| WO | 2009/123799 | 10/2009 |
| WO | 2010065052 | 6/2010 |
| WO | 2011/137264 | 11/2011 |

OTHER PUBLICATIONS

Jeon et al., "Nonintrusive, noncontacting frequency-domain photothermal radiometry and luminescence depth profilometry of carious and artificial subsurface lesions in human teeth" J. Biomed. Opt. 9(4), Jul. 1, 2004.*

Rohling et al., "Mismatched-Filter Design for Periodical Binary Phase Signals", IEEE Transactions on aerospace and electronic systems, vol. 25, No. 6, Nov. 1989.*

PCT International Search Report. PCT/CA2012/050035. Completed Jun. 13, 2012.

* cited by examiner

SYSTEMS AND METHODS FOR THERMOPHOTONIC DYNAMIC IMAGING

CROSS-REFERENCE TO RELATED APPLICATION

This application is a National Phase application claiming the benefit of PCT/CA2012/050035 filed on Jan. 20, 2012, in English, which further claims priority to U.S. Provisional Application No. 61/471,772, titled "SYSTEMS AND METHODS FOR THERMOPHOTONIC DYNAMIC IMAGING" and filed on Apr. 5, 2011, the entire contents of which are incorporated herein by reference.

BACKGROUND OF THE INVENTION

This invention relates to systems and methods of non-destructive subsurface imaging. More particularly, this invention relates to systems and methods for thermophotonic imaging.

Thermographic and thermophotonic imaging methods have found widespread use in applications such as non-destructive testing of various materials and biomedical diagnostic imaging. While numerous methods have been developed and described in the literature, most solutions proposed to date have relied on methods involving single frequency analysis of amplitude and phase images. Such methods, while well suited for some specific applications, often fail in applications that demand higher sensitivity. Another disadvantage of known thermographic and thermophotonic imaging methods is the use of low speed imaging techniques, which can place significant limitations on depth and/or spatial resolution.

Accordingly, despite the existence of a number of thermographic and thermophotonic imaging modalities, there remains a need for imaging solutions that deliver higher sensitivity, lower detection limit, increased speed, and improved depth resolution. In industrial quality control, there is a need for fast and reliable monitoring of substrate integrity and process-induced defects during manufacturing and component reliability testing, for example in identifying subsurface cracks and delaminations in automotive and aerospace components and surface coatings, respectively. In oral health care, there is a need to have an imaging system that can image an entire tooth surface or group of teeth so as to provide the oral health care provider with the location of dental caries or defects in teeth and or dental materials.

As compared to conventional thermographic imaging, which monitors contrast due to thermal and/or mechanical property inhomogeneities of materials (thermographic contrast), thermophotonic imaging, in addition to thermographic contrast, involves amplified contrast due to optical property inhomogeneities. Both modalities are based on the generation and detection of (photo)thermal waves in a sample.

SUMMARY

Systems and methods for improved thermophotonic imaging are provided in which both amplitude and phase image information is obtained with a high signal to noise ratio and depth-resolved capabilities. Image data obtained from an imaging camera is dynamically averaged and subsequently processed to extract amplitude and/or phase image data. The system may be configured for a wide range of imaging modalities, including single frequency modulation (thermophotonic lock-in imaging), Thermal-Wave Radar imaging or Thermophotonic Radar imaging involving chirp modulation, and Binary Phase Coded Modulation. Such imaging modalities may find application in many diverse areas, including non-destructive testing and biomedical diagnostic imaging including the imaging of teeth and monitoring changes in the tooth over time which are due to pathology such as dental caries or erosion.

In a first aspect, there is provided a method of performing thermophotonic imaging, the method comprising the steps of: providing a sample; providing an optical source having a wavelength selected to generate photothermal radiation within the sample; providing an imaging camera with an optical bandwidth selected for detection of the photothermal radiation; generating a reference waveform comprising a plurality of modulation cycles; producing a modulated optical beam by modulating an intensity of an optical beam emitted by the optical source according to the reference waveform; illuminating the sample with the modulated optical beam; imaging the photothermal radiation with the imaging camera; recording a plurality of dynamically averaged image frames at time offsets corresponding to different values of the reference waveform; and processing the dynamically averaged image frames and the reference waveform to obtain an image relating to the photothermal radiation.

The dynamically averaged image frames may be obtained according to the following steps: recording a plurality of image frames at times corresponding to different values of the reference waveform; repeating, one or more times, the step of recording the image frames at times corresponding to different values of the reference waveform, and dynamically averaging the recorded images for each the different value of the reference waveform, thereby obtaining dynamically averaged image frames.

The step of recording the plurality of image frames at different values of the reference waveform may comprise recording the plurality of image frames over a single modulation cycle/correlation period, and may be obtained over more than one modulation cycle, where a frame acquisition rate of the imaging camera may less than a modulation frequency of the reference waveform.

The method may further comprise the step of recording, for each image frame of the plurality of image frames, a substantially instantaneous value of the reference waveform, and may further comprise generating a quadrature waveform based on the reference waveform, and recording, for each image frame of the plurality of image frames, a substantially instantaneous value of the quadrature waveform.

An integration pulse train may be generated comprising a series of pulses, wherein each pulse is generated at a time at which an image frame is acquired by the imaging camera, wherein the step of generating of the reference waveform is triggered according to the integration pulse train. The integration pulse train may be generated by the imaging camera.

A flag pulse train may be generated comprising a series of pulses, wherein each pulse is generated at a commencement of a given modulation cycle/correlation period, and identifying one or both of a beginning and an end of the given modulation cycle/correlation period according to the flag pulse train. A modulation frequency of the reference waveform may be greater than approximately 0.01 Hz.

The reference waveform may comprise a single frequency and wherein the image is obtained by lock-in processing, and the step of processing the dynamically averaged image frames and the reference waveform may comprise, for each pixel in the image frame, performing the steps of: multiplying the dynamically averaged image frames by the reference waveform to obtain in-phase product values; and summing the in-phase product values to obtain an in-phase sum; generating a quadrature waveform based on the reference waveform; multiplying the dynamically averaged image frames by the quadrature waveform to obtain phase-shifted product values; and summing the phase-shifted product values to obtain a phase-shifted sum.

The image may be an amplitude image, and wherein the processing further comprises calculating a magnitude of a complex quantity based on the in-phase sum and the phase-shifted sum. The image may be a phase image wherein the processing further comprises: calculating a phase angle of a complex quantity based on the in-phase sum and the phase-shifted sum.

The reference waveform may comprise multiple frequency components, and the reference waveform may comprise a frequency chirp and may be a binary phase coded waveform.

The image may be a cross-correlation peak amplitude image obtained by the steps of: obtaining a complex cross-correlation signal of the reference waveform and each pixel of the dynamically averaged image frames; and determining, for each the pixel, a peak amplitude value of a peak in a real part of the cross-correlation signal.

The image may be a cross-correlation peak delay image obtained by the steps of: obtaining a complex cross-correlation signal of the reference waveform and each pixel of the dynamically averaged image frames; and determining, for each the pixel, a delay of a peak in a real part of the complex cross-correlation signal.

The image may be a cross-correlation phase image obtained by the steps of: obtaining a first complex cross-correlation signal of the reference waveform and each pixel of the dynamically averaged image frames; obtaining a second complex cross-correlation signal of a quadrature waveform and each pixel of the dynamically averaged image frames, wherein the quadrature waveform is based on the reference waveform; forming a complex quantity comprising a real portion of first complex cross-correlation signal and a real portion of the second complex cross-correlation signal; and obtaining the phase image by determining, for each pixel, a phase angle of the complex quantity at a pre-selected time delay.

The sample may be selected from the group consisting of automotive components, aerospace components, an optical material, a laser material, a biomedical material, and a biological tissue.

The sample may be a material comprising one or more of a subsurface crack and a delamination. The sample may be an unsintered component in a green state.

The method may further comprise the step of determining a case hardness depth.

The sample may be a dental sample, tooth sample or whole groups of teeth. The method may further comprise the step of analyzing the image to determine one or more of a presence and a location of demineralization, erosion or dental caries in the dental or tooth sample. The method may further comprise the step of monitoring an evolution of one or more of demineralization, erosion and dental caries by comparing the image to one or more other images. The sample may be a dental or medical instrument and may be selected from the group consisting of endodontic instruments, catheters and other indwelling instruments.

The wavelength may be selected to lie within a range of approximately 600 nm to 2000 nm. The imaging camera may be selected to have a spectral response overlapping with at least a portion of the mid-infrared spectrum.

In another aspect, there is provided a system for performing thermophotonic imaging, the system comprising: an optical source having a wavelength selected to generate photothermal radiation within a sample; an imaging camera with an optical bandwidth selected for detection of the photothermal radiation, wherein the imaging camera is configured to acquire image frames a given frame rate and output an integration pulse train comprising a series of pulses, each pulse corresponding to a time at which an image frame is acquired by the imaging camera; a waveform generating system for generating a reference waveform, wherein an output of the waveform generating system is connected to an input of the optical source for modulating an intensity of an optical beam emitted by the optical source; a processor programmed to dynamically average image frames obtained by the imaging camera, and to process the dynamically averaged image frames, the reference waveform and a quadrature waveform based on the reference waveform, to provide one or more of an amplitude image and a phase image; and a memory for storing dynamically averaged image frames.

A modulation frequency of the reference waveform may be greater than approximately 0.01 Hz. The imaging camera may comprise a frame acquisition rate that is less than a modulation frequency of the reference waveform. The wavelength may lie within approximately 600 nm to 2000 nm. A spectral response of the imaging camera may overlap at least a portion of the mid-infrared spectrum.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
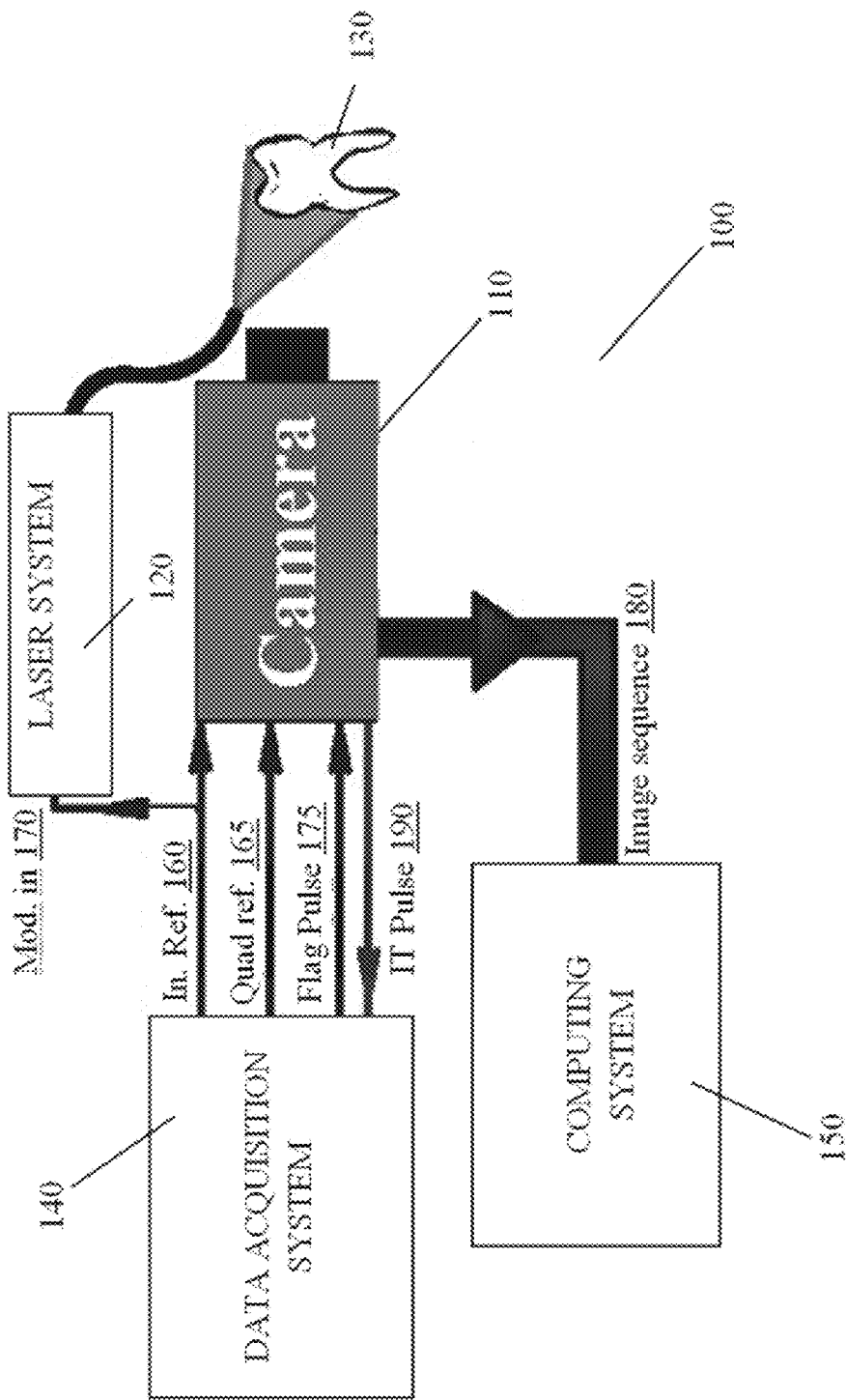
FIG. 1 shows of a system that may be employed for thermophotonic imaging.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "thermophotonic imaging" relates to the generation of images based on thermal infrared photons emitted from surface and subsurface regions of opaque or non-opaque matter, resulting from photothermal excitation of a sample with a light source such as a laser. The emitted infrared photons carry optical absorption information at the excitation wavelength as well as at the detection spectral band determined by the spectral response of the infrared imaging detector. The case of optically opaque samples, conventionally known as "infrared thermographic imaging", which involves only thermal properties, is understood to be incorporated by implication in the opaque limit of thermophotonic imaging. As compared to conventional thermographic imaging which monitors contrast due to thermal and/or mechanical property inhomogeneities of materials (thermographic contrast), thermophotonic imaging, in addition to thermographic contrast, involves amplified contrast due to optical property inhomogeneities. Both modalities are based on the generation and detection of (photo)thermal waves in a sample.

Embodiments described below provide systems and methods for improved thermophotonic imaging. In a first embodiment, a system and method is provided in which photothermal image data are dynamically averaged and subsequently processed to determine both amplitude and phase image information with high signal to noise ratio. The system may be configured for a wide range of imaging modalities, including, but not limited to, single frequency modulation (thermophotonic lock-in imaging or thermophotonic lock-in imaging), chirp modulation (thermal-wave radar imaging or thermal wave radar imaging), and binary phase coded modulation (Binary Phase Coding imaging or binary phase code imaging).

FIG. 1 shows a schematic of a thermophotonic imaging system 100 that may be utilized for a number of different imaging modalities. System 100 includes imaging camera 110 for detecting and imaging thermophotonic radiation, laser 120 for exciting a photothermal response in a sample 130, data acquisition system 140, and computing system 150 that is interfaced to camera 110 and/or data acquisition system 140 (in the example embodiment shown in FIG. 1, computing system 150 is directly interfaced to camera 110 for reading both image data and data acquisition header data in image frames, as described further below). Sample 130 may be positioned using a sample positioning device, such as a 3-axis (XYZ) sample positioning system (not shown).

Laser 120 is modulated to produce a modulated optical beam that is directed onto the surface of an extracted sample tooth 130, which in turn leads to the generation of photothermal radiation from sample 130 that is subsequently detected by imaging camera 110. In order to obtain high signal-to-noise ratio (SNR) via phase-sensitive detection, a synchronous driving and data acquisition approach is employed, in which frames outputted by imaging camera 110 are synchronized with the modulation of laser 110 for further processing.

Figure 2:
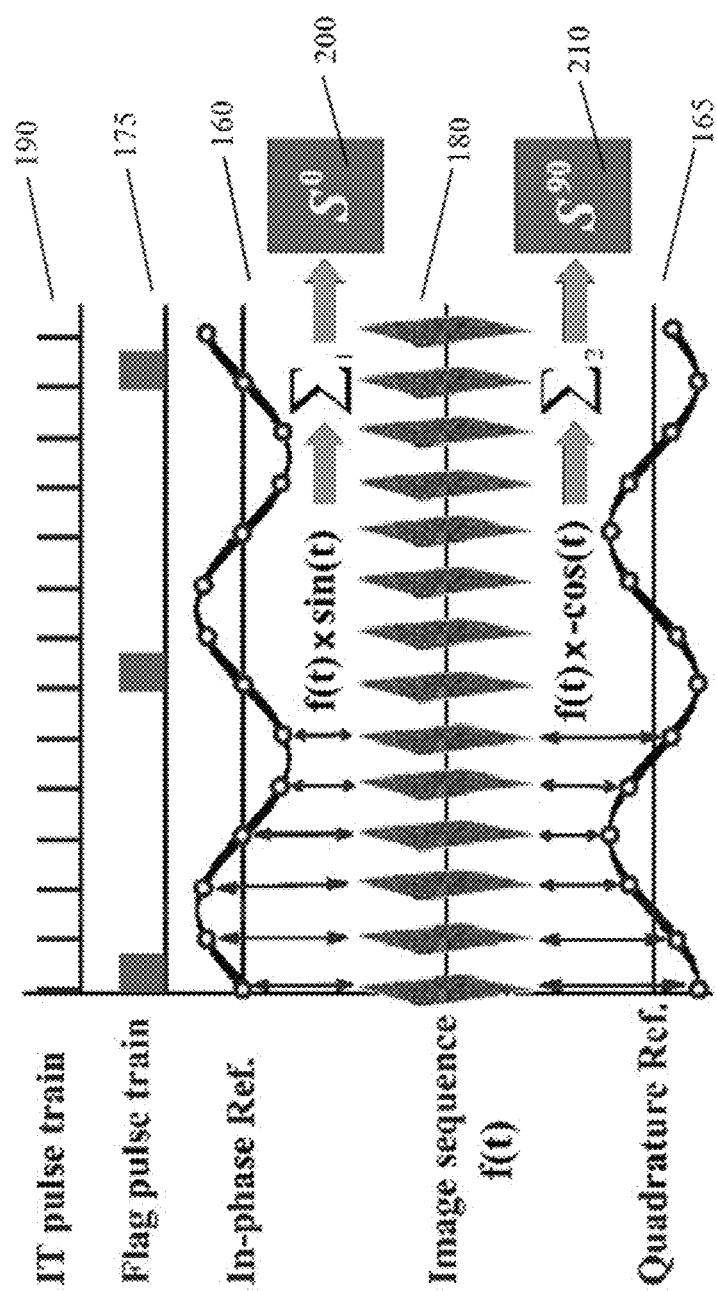
FIG. 2 illustrates a method of thermophotonic lock-in imaging.

Referring now to FIG. 2, system 100 is further described in the context of a thermophotonic imaging modality involving thermophotonic lock-in detection, which represents an illustrative yet non-limiting embodiment of an imaging modality compatible with system 100. Data acquisition system 140 generates analog in-phase reference waveform 160 and analog quadrature reference waveform 165, where quadrature waveform 165 is phase shifted by 90° relative to in-phase waveform 160. Alternatively, the quadrature reference waveform may be computed from the Hilbert Transform of the in-phase reference signal.

In-phase waveform 160 is provided to the modulation input 170 of laser system 120, (shown in FIG. 1). In response to in-phase waveform 160, the intensity of the emitted laser light is modulated, where the modulation profile of the laser intensity follows that of in-phase waveform 160 plus a DC offset.

Imaging camera 110 obtains image frames at a defined frequency as shown by integration pulse train (IT pulse train) 190 in FIG. 2. Integration pulse train 190 is provided (e.g. as a TTL pulse train) from imaging camera 110 to data acquisition system 140 to trigger the generation of in-phase waveform 160 and quadrature waveform 165 by data acquisition system 140. Integration pulse train 190 also triggers the generation of flag pulse train 175 by data acquisition system 140, where flag pulse train 175 provides a "high" pulse at the beginning of each modulation cycle, as shown in FIG. 2.

In the embodiment shown in FIG. 1, imaging camera 110 is capable of providing a header for each recorded image frame, where the header includes the measurement of two values that are measured at a time that is substantially instantaneous with the detection of an image frame. The two values are obtained from two analog signals corresponding to instantaneous values of waveforms 160 and 165. Data acquisition system 140 provides these waveforms to imaging camera 110 for inclusion of the two values in the frame header, thereby providing a measurement of their values at a time that is substantially simultaneous to the instant that the frame is captured. Values from flag pulse train 175 are also stored in the frame header to allow for the determination of the beginning of each waveform period, which is used for averaging purposes as further described below. It is to be understood that the direct interfacing of computing system 150 to camera 110, as shown in FIG. 1, is but one of many different possible system implementations. In other embodiments, computing system may be interfaced to camera 110 and/or data acquisition system 140 for synchronous acquisition of both image and modulation waveform instantaneous data, as further described below.

During image acquisition, computing system 150 reads image frames from imaging camera 110 via image sequence 180, and queries the frame headers until it finds a frame whose flag pulse train is "high" (the beginning of a modulation cycle). After a "high" pulse is detected, computing system 150 reads a sequence of frames that correspond to one complete modulation cycle, where the number of frames and delay between frame acquisition events is determined based on the frame rate of imaging camera 110 and the modulation frequency of the in-phase waveform 160. The frames are stored in a buffer (e.g. a 3D buffer) in a memory (such as computer RAM). By performing these steps, system 100 obtains a series of individual imaging frames corresponding to one modulation cycle.

To obtain an improved SNR of the acquired image frames, the above steps are repeated and the values for each frame of one complete modulation cycle are averaged in the buffer to reduce the stochastic noise. Most averaging algorithms read the signal corresponding to all recorded cycles and then initiate the averaging processes. Unfortunately, due to the huge flow of data needed to meet the bandwidth demands of the image frames, such an averaging methodology fails at high frame rates, such as those that are preferably used in the present embodiment.

Accordingly, in a one embodiment, the image frames are dynamically averaged, where the frames corresponding to one modulation cycle are collected and dynamically processed to determine a running average. Initially, a first set of image frames corresponding to a first modulation cycle are collected and stored in a memory location. Subsequently, image frames are obtained for a second modulation cycle, and the recorded image frame values are dynamically averaged. This process is repeated for subsequent modulation cycles, with the averaging based on the number of modulation cycles that have been processed, with the result that an averaged set of image frames with improved SNR is obtained. This provides a dramatic improvement in memory management and speed, and requires significantly less sophisticated computer hardware.

After having obtained an averaged set of image frames over a modulation cycle, the averaged frame sequence, shown at 180 as f(t) in FIG. 2, corresponding to averaged image frames, is processed to obtain amplitude and phase images. This is performed by weighting each pixel in the image for each frame obtained, where the pixel value is weighted once by the in-phase reference signal 160 and once by the quadrature reference signal 165 in two separate channels. The weighted sequences are then separately summed to get the $S^0$ and $S^{90}$ images, as shown in steps 200 and 210 of FIG. 2, respectively. Finally, using equation 1 for each pixel the amplitude and phase images are calculated:

$$A=\sqrt{(S^0)^2+(S^{90})^2} \text{ and } \Phi=\arctan(S^{90}/S^0) \quad (1)$$

Computing system 150 may be programmed with a signal acquisition and/or processing program for processing the data received from imaging camera 110 and/or data acquisition device 140, and for performing the aforementioned averaging steps and calculation of the amplitude and phase images. For example, generic data processing programs may be provided commercially or created for specific applications associated with the thermophotonic imaging modalities disclosed herein. A suitable programming medium for the creation of such a program is the LabView environment. This environment provides a flexible platform for adapting the imaging software to non-destructive/diagnostic groups of equipment (set-ups) for application specific to particular materials and configurations (e.g. engineering materials NDT, biomaterials diagnostics, dental caries imaging).

Unlike lock-in thermography, which is mostly used in non-destructive testing of metals and other opaque structural materials at very low modulation frequencies (on the order of 0.01 Hz or so), and in which low camera frame rates (usually 20 fps), and high optical excitation power (high SNR signal) are used without averaging, in thermophotonic imaging of biological samples and industrial materials with defects very close to surface, one may need high frequency thermal waves and low optical excitation power (poor SNR signal) to meet safety criteria. Therefore, in such cases, it can be advantageous to employ very high camera frame rates and a real-time averaging methodology, as provided, according to the present embodiment.

While the above embodiments provide exemplary systems and methods for obtaining thermophotonic images, it is to be understood that the systems and methods may be varied without departing from the spirit and scope of the aforementioned embodiments. For example, referring now to FIG. 1, although system 100 is shown as comprising computing system 150 and data acquisition system 140, these elements of the apparatus may be provided in a number of different formats. Computing system 150, which comprises a processor and a memory, may be directly integrated with data acquisition system 140. For example, data acquisition system 140 may reside in total or in part on a hardware card housed within an apparatus that also comprises a processor and a memory.

Laser system 120 may further comprise additional subcomponents or subsystems such as, but not limited to, a laser diode emitter, laser driver, fiber coupled output, collimator, and thermoelectric cooler and controller. In one exemplary embodiment, laser system 120 has two laser diodes so as to provide improved optical contrast of a type of sample through large differential absorption (for example, 808 nm and 1120 nm). Typically, laser diodes are mounted on thermoelectric coolers and the diode assembly is fixed on an air cooled heat sink through a heat conductive thermal pad. The laser light may be delivered to the sample through an optical fiber and a collimator. A collimator and/or spatial filter may be provided to maintain a relatively uniform optical intensity on the interrogated surface. The thermoelectric controller provides the cooling power to the thermoelectric coolers and controls the temperature of the laser diode. The laser driver may be employed to provide the electrical power needed to operate the laser diode and can modulate the laser light intensity according to the analog modulation signal it receives at its "mod in" terminal.

Furthermore, it is to be understood that optical source need not be a coherent light source such as a laser, but may instead be an incoherent source such as a LED, provided that sufficient optical intensity is achieved to obtain a measurable thermophotonic image signal. With the advent of high-power LEDs, one may employ a high-power infrared LED or LED array in place of a laser source. LED arrays are significantly less expensive than laser sources and generally do not require complicated cooling systems. This strategy can be used because in the proposed methodologies it is the thermal (conductive and radiative) response from the sample that is investigated, and not the purely optical response.

As noted in the example embodiment provided above, data acquisition system 140 is capable of generating and/or providing waveforms 160 and 165 in response to the integration pulse train 175 generated by the imaging camera. In a non-limiting example, data acquisition system may be a DAQ board such as National Instrument Multi Data acquisition device (NI USB-6229 BNC), and the like, which may be directly integrated with or housed within computing system 150. Such a multifunction data acquisition (multi-DAQ) system can generate and acquire analog signals simultaneously and has two independent counters and 48 digital I/O channels for synchronization applications. The data acquisition system may be connected to the computer with a USB port and may be configured to communicate with other devices through BNC connections.

Computing system 150 may be interfaced to imaging camera 110 through an interfacing device such as a networking card. For example, the GigE network PCI card may be employed to provide a suitable interface between the camera and the computer for rapidly transferring image frames to the memory of the computing system 150 according to the GigE standard.

As noted above, the sample 130 and/or laser source may be positionable relative to one another. For example, a sample positioning system may be provided that consists of one or more single axis translation stages mounted to move the sample relative to the incident laser beam in X, and optionally Y and Z directions. A rotational stage may be added to this assembly to assist in the placement of the sample in the focal plane of the camera.

While system 100 as disclosed above is capable of averaging numerous modulation cycles of the signals before processing them, it is also possible to perform that averaging based on the computed amplitude and phase images as opposed to the image frames.

Such an embodiment may be achieved by reading, at a given point in time, a sequence of frames corresponding to one or more modulation cycles, processing the image frames as outlined above, and calculating the desired diagnostic images (i.e. amplitude, phase) and then repeating these steps and averaging the amplitude and phase images. While this "processing, then averaging" mode is less effective in eliminating the stochastic noise than the "averaging, then processing" strategy, it requires less sophisticated triggering/synchronization equipment. For example, this embodiment involves the simplification of the control section of the camera and signal processing system with respect to triggering. This approach will yield non-triggered, yet synchronized, data arrays resulting in an image of somewhat compromised quality.

Furthermore, although system 100 is shown in FIG. 1 in which the waveforms 160, 165 and 175 are provided by data acquisition system 140 to imaging camera 110 for incorporation of the substantially instantaneously measured values into the frame header, it is to be understood that the values may be provided according to alternative system implementations. Such embodiments may be useful in cases where imaging camera 110 is not equipped or configured for the incorporation of a header in each image frame. For example, in one non-limiting embodiment, the waveforms 160, 165 and 175 may be directly provided to computing system 150 by data acquisition system 140, optionally along with integration pulse train 190 from imaging camera 110 for triggering. Provided that the relative time delay between the reception of the waveforms and the generation and/or reception of image frames may be determined (for example, by measuring a delay between system components), the appropriate values of the waveforms corresponding to the measurement of image frames may be determined.

Alternatively, the waveforms 160, 165 and 175 may be generated directly by computing system 150 (optionally triggered by integration pulse train 190 provided by imaging camera 110), and the correlation between the appropriate values of the waveforms and the acquisition of image frames may be determined based on a known system delay. These embodiments may be applied to the system shown in FIG. 1, or in the system described above in which the synchronization of triggering is not necessary.

In one embodiment, imaging camera 110 is an infrared imaging camera that is sensitive in the infrared spectrum. Imaging camera 110 may incorporate the necessary optical components for the collection and detection of photothermal radiation, or one or more of the optical components may be externally mounted or otherwise provided. For example, imaging camera may include an extension tube supporting an objective lens.

In one exemplary embodiment, imaging camera 110 is a focal plane array (FPA) mid-infrared camera. A suitable but non-limiting example of such a camera is the Cedip Titanium 520M (France), which has a spectral range of 3.6-5.1 µm and maximum frame rate of 175 Hz at full frame. The camera's detector array consists of 320×256 Indium Antimonide (InSb) elements with element size of 30×30 µm². An extension tube and a objective lens (such as Cedip MW50 L0106, a 50-mm-focal-length lens) may be employed to obtain a magnification of (for example, of unity) relative to the interrogated surface of sample 130.

While the mid-infrared camera may be preferred for obtaining optimum results for some sample types, one may also employ less expensive near- or far-infrared cameras, generally with the performance trade-off of a reduced signal-to-noise ratio. However, the low signal to noise ratio can be mitigated, at least in part, by a number of methods such as, for example, increasing the number of averages, using matched filtering signal processing methods (thermal wave radar and binary phase code) described above, increasing the optical source intensity, increasing the camera integration time, and/or improving the optical collection efficiency. It is expected to be more effective to employ a far infrared camera to capture thermal infrared photons due to the peak of the blackbody radiation being located in that spectral range, although the spectral transmissivity of the interrogated material must also be considered in determining the thermal infrared photon emission flux to the camera following self-absorption.

Furthermore, in selected embodiments, uncooled imaging cameras may be employed to simplify the system and/or reduce cost. The cooling system of a camera is one of the factors that make the camera expensive. Uncooled cameras are significantly less expensive but at the same time less sensitive. This problem can be solved by increasing compensation for a reduced performance by using one of the mitigating methods described above.

In another embodiment, a camera with a lower frame acquisition rate may be employed. While lowering the frame rate does not significantly affect the performance of thermophotonic lock-in imaging, the sampling period can be critical in matched filtering methodologies (thermal wave radar and binary phase code) as it determines the depth resolution. Two strategies can be followed to overcome the depth resolution limitation while using a low-grade (low frame rate) camera.

Figure 16:
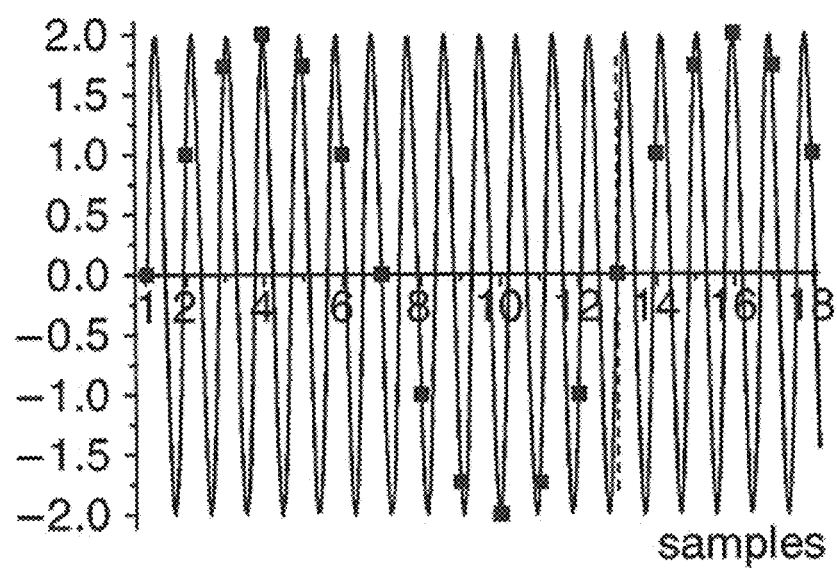
FIG. 16 illustrates the method of asynchronous undersampling for lower frame acquisition rate imaging cameras.

In a first method, synchronous/asynchronous undersampling may be employed, whereby the frame rate is chosen such that the data are captured from many modulation cycles instead of just one. This embodiment is illustrated in FIG. 16. Although this sampling strategy increases the total sampling duration, this alternative implementation enables the use of a lower-grade camera to access image depth resolution commensurate with that of the foregoing high-grade camera. The combination of critical undersampling determination with the desired thermal-wave depth penetration, and their software implementation thus provide a unique and important benefit to system performance.

Figure 13:
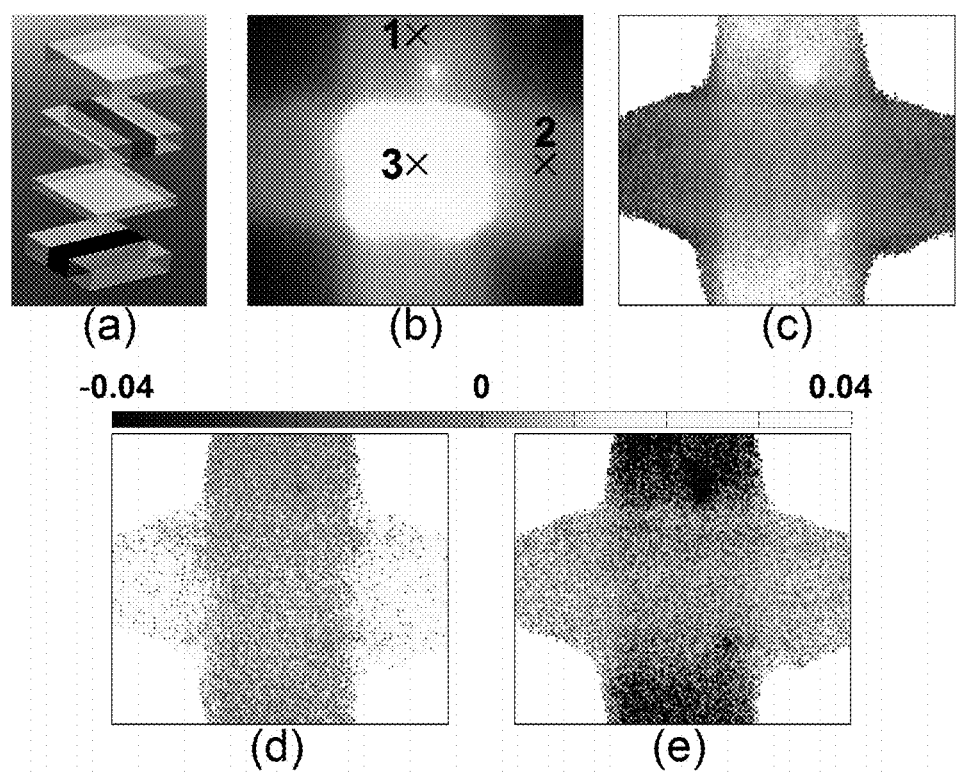
FIG. 13 (a) Exploded view of the cross-shaped sample simulating two absorbers at different depths. Conventional LIT (b) Amplitude and (c) phase image. binary phase code peak delay time image matched to the camera temporal data of (d) point 1 and (e) point 2, as indicated in part (b), using a 3-bit [1 1-1] code.

The undersampling frequency ($f_s$) can be determined as follows:

$$f_s = f_{lock-in}/[m+(1/n)] \tag{1a}$$

where $f_s$ is the undersampling frequency, $f_{lock-in}$ is the desired lock-in frequency (or alternatively, chirp/binary phase code repetition rate), m is an integer number and is called the order of undersampling, and n is the number of frames per correlation period. In FIG. 13, m=1 and n=12, that is one frame is captured in every m=1 modulation cycle and at the end of the process the sampled modulation cycle (i.e. correlation period) consists of n=12 frames[8].

In a second method, artificial oversampling is performed as per the sampling theorem, which states that if the Fourier transform of a function h(t) is zero for all frequencies above a certain frequency $f_c$, then the continuous function h(t) can be uniquely determined from a knowledge of the sampled values. So, if the function is sampled at $T=\frac{1}{2}f_c$, then one can use the expression below to reconstruct the waveform at any sampling/frame rate:

$$h(t) = T \sum_{n=-\infty}^{\infty} h(nT) \frac{\sin(2\pi f_c(t-nT))}{\pi(t-nT)} \tag{2}$$

The methodology is also known as "Sinc interpolation". Therefore, one can use a low frame rate camera and then use Sinc interpolation to improve the sampling resolution. The determination of cut off frequency, $f_c$, satisfying the requirement of a predetermined thermal diffusion length (depth resolution) may be performed according to equation 5, as further described below.

An alternative option for an infrared camera for use with system 100 may be provided by modifying a digital visible spectrum camera such as a commercial digital camera or a webcam. Such cameras may be modified to be sensitive in the near-infrared spectral region by removing the infrared filter and then inserting an infrared band pass filter in the optical path of the detector array. The performance degradation that is likely based on use of such a camera may be mitigated, at least in part, by the methods listed above.

An alternative option for an infrared camera for use with system 100 may be provided by modifying a digital visible spectrum camera as noted above and using methods listed above to handle performance degradation. The output from this camera would be in color with color linked to the status of the specimen under examination. In another embodiment, the camera may be a monochrome camera, and the defect region may be displayed in a unique false colour. The defect may be identified automatically by image processing (for example, using known methods to identify regions of an image based on intensity and/or the presence of a border feature). Alternatively, the defect may be identified in response to input from a user or operator viewing the image.

In one example embodiment, the defect size may be correlated with its displayed colour. For example, an area where there is a large defect may be displayed (and optionally imaged) in red while an area which is sound or healthy may be displayed (and optionally imaged) in green. An area where the defect is small can be displayed (and optionally imaged) in yellow. This gradation from green to yellow to red would help the operator visually understand the relative size of the defect, and in the case of dental imaging, would assist in visually assessing the severity of any detected defects.

Another imaging modality that is suitable with system 100 employs thermal-wave radar imaging. In thermal wave radar imaging chirp modulation is used instead of the aforementioned method of single frequency modulation (thermophotonic lock-in) modality and the matched filtering signal processing method is employed to increase the SNR. For non-opaque targets, this method is referred to "thermophotonic radar imaging". It should be noted that this methodology is completely different from thermophotonic lock-in imaging and is a depth selective method as opposed to a depth integrated method in thermophotonic lock-in imaging. As a result, thermal wave radar not only probes deeper into a sample, but also provides improved resolution of details and faster image acquisition due to its high SNR (i.e. requires less averaging).

FIG. 3(a) explains the thermal wave radar imaging method graphically. As in the thermophotonic lock-in method, a sequence of image frames are acquired in combination with the values indicating the values of the waveforms 160, 165 and 175. The role of the flag pulse train 175, the integration pulse train 190, and the averaging method, are the same as in the thermophotonic lock-in method described above. However, unlike the case of thermophotonic lock-in in which one modulation cycle is being averaged, it is one chirp cycle of the chirped reference signal 250 that is averaged in the thermal wave radar imaging or the thermophotonic radar imaging method.

FIG. 3(b) depicts the signal processing block diagram of thermal wave radar imaging according to the cross-correlation (CC) theory (matched filtering theory):

$$CC(\tau) = \epsilon \times \mathfrak{I}^{-1}\{REF(\omega)^* S(\omega)\} \quad (3)$$

where $REF(\omega)$ 300 and $S(\omega)$ are the Fourier transforms of the reference/modulation signal ($Ref(t)$) and the highly noised photothermal signal ($s(t)$), $\epsilon$ is the emissivity and $\mathfrak{I}^{-1}$ and * denote the inverse Fourier transform and complex conjugate operators, respectively. In matched filtering, the role of chirped modulation is to compress the energy delivered by the chirp into a narrow correlation peak which enables imaging with high axial resolution. The result is a reduction in the width of the CC main lobe (peak) and an increase in the amplitude of the peak as the area below it needs to be conserved. In the case of a linear frequency sweep, the signal-to-noise ratio (SNR) gain factor of the ideal matched filter is equal to the time-bandwidth product of the chirp. Theoretical and experimental studies have shown that this increase in SNR also holds in the photothermal fields.

While the amplitude of the CC peak relies strongly on the amplitude of the received signal, its location in the delay time axis ($\tau_p$) is linked to the depth of the signal source. One can further develop this concept by calculating the CC phase (schematically in FIG. 3(b)) and find:

$$\theta_{CC} = \frac{\mathscr{R} \times \mathcal{J}^{-1}\{REF(\omega)^* S(\omega)\}}{\mathscr{R} \times \mathcal{J}^{-1}\{[-i\operatorname{sgn}(\omega)REF(\omega)]^* S(\omega)\}} \quad (4)$$

where $\operatorname{sgn}(\omega)$ and $i$ are the signum function and standard imaginary unit, respectively. The expression inside the squared bracket is the Fourier transform of the quadrature reference signal. The significance of CC phase is that according to equation 4 the emissivity is cancelled out and as a result the CC phase is an emissivity-normalized quantity.

In light of the above, after the averaging step, the temporal signal from each pixel is processed according to FIG. 3(b). Initially, the Fourier transform of reference Ref(t) 300, quadrature signal (i.e. Hilbert transformed reference signal), and averaged photothermal signal S(t) 305 are obtained at 310, 315 and 320, respectively. The complex conjugate 325 of the reference spectrum is then multiplied by the spectrum of the photothermal signal which is proportional to the emissivity, and the inverse Fourier transform is obtained at 330, the real part of which generates cross-correlation signal 335. Similarly, the complex conjugate 340 of the Hilbert transform of the reference spectrum is multiplied by the spectrum of the photothermal signal which is also proportional to the emissivity, and the inverse Fourier transform is obtained at 345. The phase signal 360 is then provided by taking, as its real part, the real part 350 of the inverse transform 330, and as its imaginary part, the real part 355 of inverse transform 345.

From these calculated signals, contrast parameters may be generated and displayed as images. The following are a non-limiting list of parameters that may be provided for generating images:

(a) the cross-correlation amplitude image, in which the contrast parameter is the amplitude of the cross-correlation peak;
(b) the cross-correlation peak delay time image, in which the contrast parameter is the location of the cross-correlation peak in the delay time axis ($\tau_p$); and
(c) the emissivity normalized cross-correlation phase image, in which the contrast parameter is the phase value at zero delay time calculated from equation 4.

In one example embodiment, one or more of these images, namely the cross-correlation amplitude image, the cross-correlation peak delay time image, and/or the emissivity normalized cross-correlation phase image, are generated and employed to infer information about the sample 130.

The above images are to be contrasted with known methods of processing thermophotonic image data. In the Radar sciences, matched filtering has been used since the early 1940s to detect pre-known (deterministic) signals within highly noised channels and to augment the range resolution. In 1986 Mandelis et al. in a series of papers introduced this method to the photothermal field through the mirage (photothermal beam deflection) effect[4(a-c)]. Recently, Mulaveesala et al.[5] and Tabatabaei and Mandelis[6] (Thermal-Wave Radar) have applied this methodology to imaging in the photothermal field. For example, in the method of Mulaveesala et al.[5] (which is based on a pulse compression technique), a completely different approach is taken to calculate a so-called "phase image" from a chirped reference signal. Instead of processing the phase image according to all components in the frequency domain as in equation 4, the method of Mulaveesala et al. is based on demodulating the camera signal at a specific frequency. This method is completely different from the inventive methods disclosed herein and has long been used in the field of Pulse Phase Thermography[9]. More specifically, the phase image of Mulaveesala et al. is obtained by computing the Fourier transform of a pixel signal, and the value of this Fourier transform at the desired frequency will be a complex number. The phase is obtained by calculating, based on this complex frequency, the phase value $\tan^{-1}$ (imaginary part/real part). In fact, those skilled in the art will appreciate that this approach of phase calculation was first introduced in Pulse Phase Thermography[9]. This phase value is the phase of a single frequency thermal-wave; it is not a true matched filtering/cross-correlation calculation.

Figure 3:
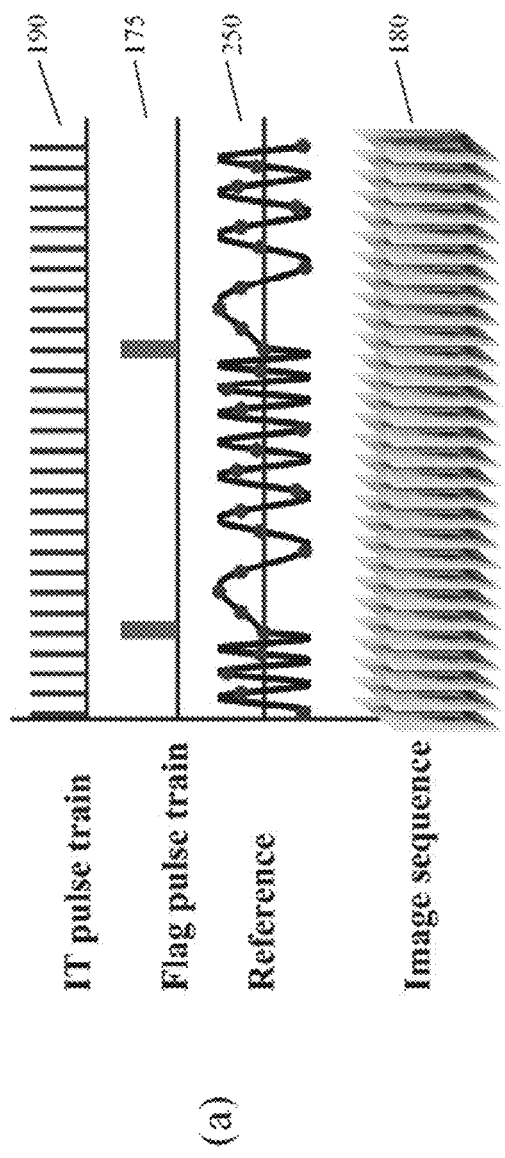
FIG. 3 illustrates thermal-wave radar imaging, where (a) shows the waveforms and frames captured, and (b) provides a flow chart illustrating the method.
Figure 3:
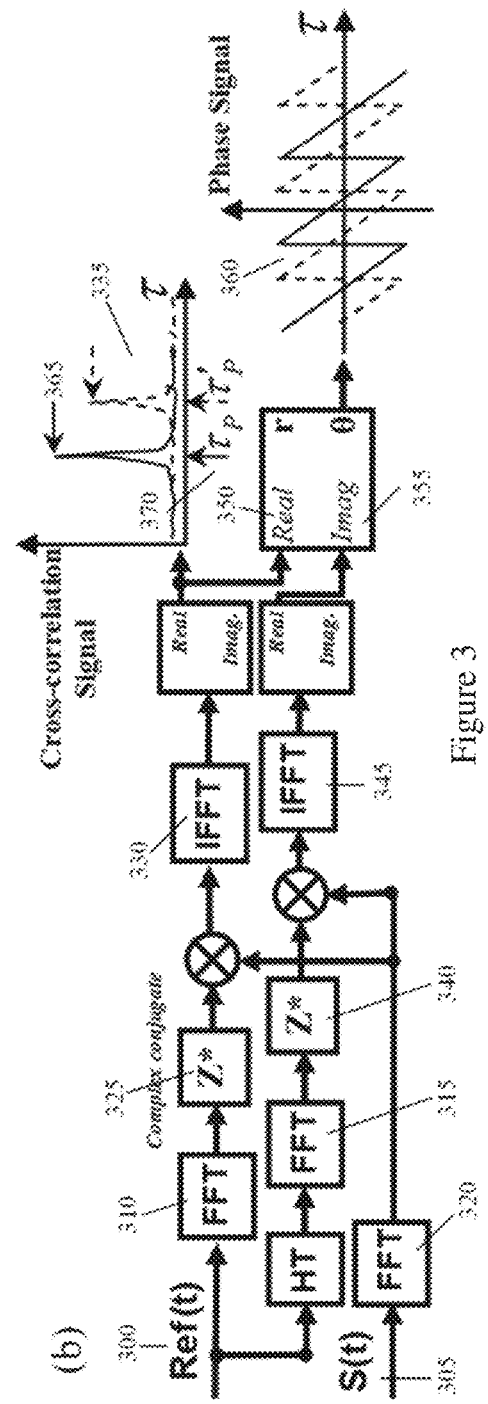

In contrast, according to the methodology disclosed herein, which is shown in the block diagram of FIG. 3, the complex conjugate phase is calculated using all the frequency components of the chirp through cross-correlation/matched filtering of reference and quadrature signals. In summary, the phase images that are obtained according to the methods of Mulaveesala et al. result in depth integrated images over a thermal diffusion length controlled by the modulation frequency, in contrast to the method disclosed herein which results in depth-resolved (or depth-selective) imaging. The method disclosed herein is the result of correlation processing, otherwise known as "matched filter compression". As will be seen in the single frequency image of FIGS. 10d and 10e, compared to the matched filter compression generated images of FIGS. 10b and 10c, this difference in approach has huge contrast enhancement implications in favor of matched filter compression.

Furthermore, unlike known imaging modalities such as those disclosed by Mulaveesala et al., the present embodiments utilize thermophotonic imaging, which is applicable to a wide range of imaging applications beyond opaque sample imaging applications (such as imaging of metals). In particular, and as further described below, the optical scattering and absorption properties of dental and other biomaterials introduce a non-extrapolatable factor in imaging, which cannot be readily perceived by one skilled in the thermographic imaging, as frequency ranges, wavelengths, delay times etc. are all very different and image contrast optimization is controlled by the diffusion-wave centroid determined by the thermal diffusion length and optical absorption depth (or extinction depth, in case of turbid media) according to equation 5(b) as shown below.

Embodiments provided herein also improve over known imaging modalities that employ very low frequencies, such as those typical of thermography. Such methods that rely on low frequencies may be applicable for deep subsurface metal defects, but are insufficient for thermal-wave radar in materials such as teeth and surface coatings, where high frequencies are needed for critical spatial and temporal (axial) resolution. In contrast to such low-frequency applications, the present embodiments may be employed for frequencies up to several hundred Hz via the aforementioned signal processing and data handling methods. Moreover, the embodiments disclosed herein may be adapted for use with inexpensive slower IR cameras in place of more expensive IR imaging cameras. Accordingly, the embodiments provided herein are especially adapted for thermophotonic imaging of non-opaque solids, but are also valid in the limit of opaque targets upon appropriate parameter adjustment.

The aforementioned embodiment, in which chirp modulation is employed in thermal wave radar imaging and thermophotonic radar imaging, provides a reduction in the width of the cross-correlation peak. This not only improves the depth resolution and allows for depth-selective imaging, but also increases the height of the peak (i.e. SNR) as the area below it needs to be conserved.

In another embodiment, an alternative approach is employed in which binary phase coding is utilized instead of a chirp to obtain an improved SNR. Binary phase coding is an alternative method that uses single frequency modulation but inverts some of the modulation cycles in a prescribed manner in order to achieve this goal. The signal processing method is the same as the aforementioned thermal wave radar imaging and thermophotonic radar imaging embodiment, and uses matched and mismatched filtering to detect a signal source. However, in the case of binary phase code imaging, the modulation waveform is a binary phase coded single frequency waveform. As a result, binary phase code imaging is considered as a narrow-band detection compared to thermal wave radar imaging/thermophotonic radar imaging and experiences lower background noise level.

Figure 4:
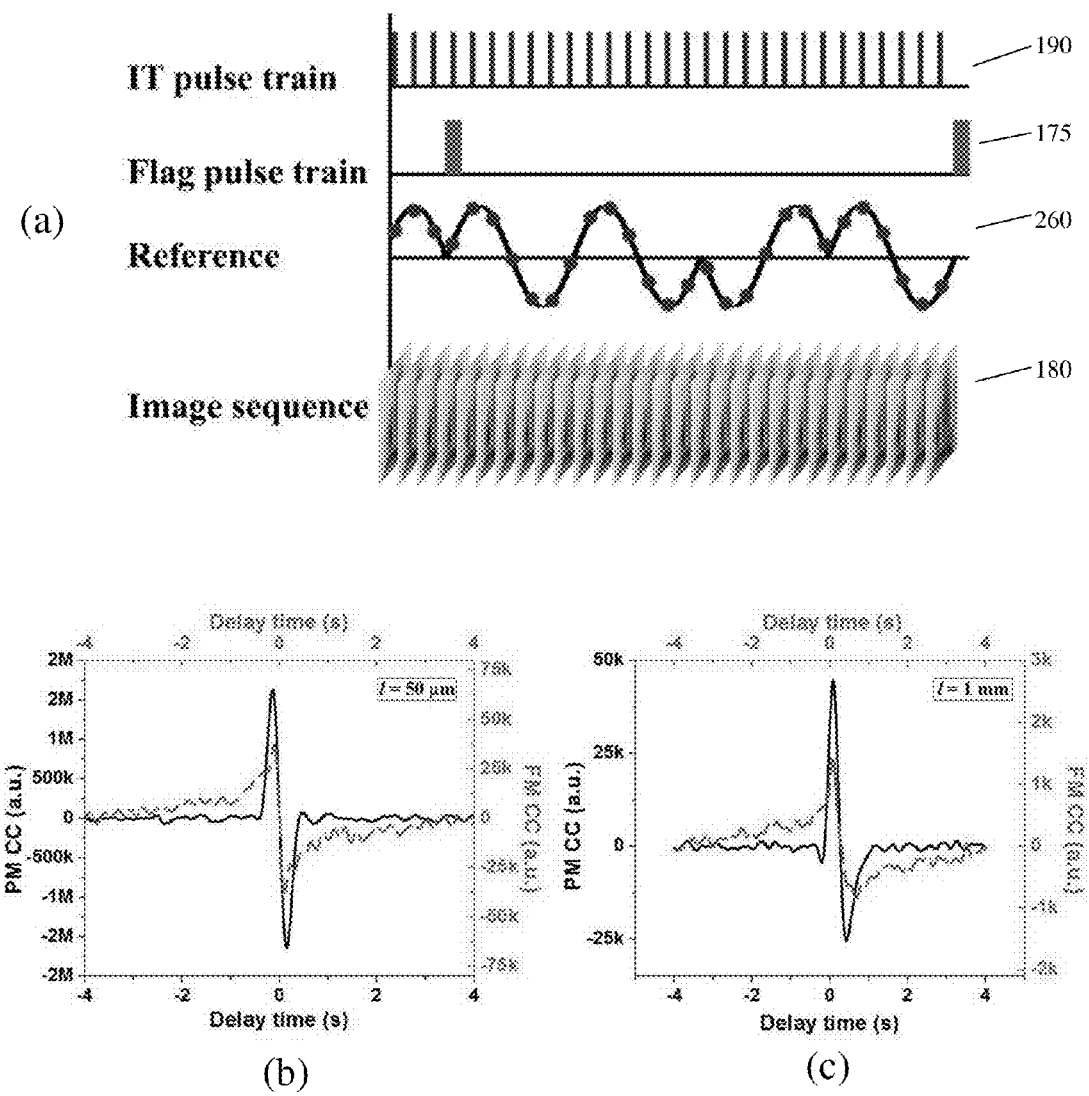
FIG. 4 (a) illustrates a method of binary phase code imaging. Theoretical simulation of CC signals using frequency (dashed) and phase (solid) modulation for absorbers at depths (b) 50 μm and (c) 1 mm below the surface using thermal and optical properties of dental enamel. Chirp: 0.1-4.9 Hz, 6.4 s; BPC: 2.5 Hz, 16 bit, 6.4 s.

FIG. 4 illustrates this method graphically for a 3-bit coded signal 260 ([1, 1, −1]) shown at reference waveform 400. The third cycle is inverted with respect to the other cycles to generate the binary phase code waveform, forming a single frequency signal that is coded according to the 3-bit sequence in Table 1.

TABLE 1

Binary phase code sequences[10].

| length N | sequence $c_k$ | | | | | | | | coefficients $w_k$ | | | | | | | | relative efficiency |
|---|---|---|---|---|---|---|---|---|---|---|---|---|---|---|---|---|---|
| 3 | 1 | 1 | −1 | | | | | | 1 | 1 | 0 | | | | | | 66.67 percent |
| 4 | 1 | 1 | 1 | −1 | | | | | 1 | 1 | 1 | −1 | | | | | 100.00 percent |
| 5 | 1 | 1 | 1 | 1 | −1 | | | | 1 | 1 | 1 | 1 | −2 | | | | 90.00 percent |
| 6 | 1 | 1 | 1 | 1 | 1 | −1 | | | 1 | 1 | 1 | 1 | 1 | −3 | | | 76.19 percent |
| 7 | 1 | 1 | 1 | 1 | 1 | 1 | −1 | | 1 | 1 | 1 | 1 | 1 | 1 | −4 | | 64.93 percent |
| 8 | 1 | 1 | 1 | 1 | −1 | −1 | 1 | −1 | 1 | 1 | 3 | 1 | −1 | −1 | 3 | −1 | 75.00 percent |
| 9 | 1 | 1 | 1 | 1 | 1 | −1 | 1 | 1 | 1 | 1 | 6 | 1 | 1 | −4 | 1 | 1 | 60.11 percent |
|  | −1 | | | | | | | |  | −4 | | | | | | | |
| 10 | 1 | 1 | 1 | 1 | −1 | 1 | −1 | | 9 | 19 | 1 | 7 | 5 | −9 | 25 | −1 | 59.66 percent |
|  | −1 | −1 | | | | | | |  | −7 | −5 | | | | | | |
| 11 | 1 | 1 | 1 | 1 | 1 | −1 | 1 | 1 | 71 | 20 | 47 | 17 | 80 | −79 | 68 | 53 | 77.47 percent |
|  | −1 | −1 | −1 | | | | | |  | −49 | 5 | −55 | | | | | |
| 12 | 1 | 1 | 1 | 1 | 1 | −1 | −1 | 1 | 2 | 1 | 1 | 2 | 1 | −1 | −2 | 1 | 88.92 percent |
|  | 1 | −1 | 1 | −1 | | | | |  | 1 | −2 | 1 | −1 | | | | |
| 13 | 1 | 1 | 1 | 1 | 1 | −1 | −1 | 1 | 2 | 2 | 2 | 2 | 2 | −3 | −3 | 2 | 96.15 percent |
|  | 1 | −1 | 1 | −1 | 1 | | | |  | 2 | −3 | 2 | −3 | 2 | | | |
| 14 | 1 | 1 | 1 | 1 | 1 | 1 | −1 | −1 | 1 | 4 | 4 | 1 | 4 | 1 | −5 | −5 | 82.29 percent |
|  | 1 | 1 | −1 | 1 | −1 | 1 | | |  | 4 | 4 | −5 | 4 | −5 | 1 | | |
| 15 | 1 | 1 | 1 | 1 | 1 | 1 | −1 | 1 | 4 | 4 | −5 | 4 | −5 | 1 | | | 86.81 percent |
|  | −1 | −1 | 1 | 1 | −1 | −1 | −1 | |  | | | | | | | | |
| 16 | 1 | 1 | 1 | 1 | 1 | 1 | −1 | 1 | 3 | 21 | 45 | 39 | 27 | 5 | −27 | 39 | 79.43 percent |
|  | −1 | 1 | −1 | −1 | 1 | 1 | −1 | −1 |  | −45 | 21 | −3 | −25 | 43 | 37 | −43 | −25 |

While the optical excitation is binary phase coded in accordance to weighting sequence $c_k$ in table 1, one can choose to use Matched Filtering (weighting sequence $c_k$ in table 1) or MisMatched filtering (weighting sequence $w_k$ in table 1) as the 300 reference signal in FIG. 3(b) to calculate the binary phase code amplitude, peak delay time, and phase images using the method illustrated in the block diagram of thermal wave radar or thermophotonic radar imaging modality (shown in FIG. 3(b)). The advantage of MisMatched filtering over Matched filtering is the significant reduction of side lobes at the expense of lower SNR[10].

The binary phase code signal, f(t), consists of a single frequency carrier, C(t), and a binary coded envelope, E(t). The signal is formed by either multiplying these components in the time-domain or alternatively by convolving their spectra in the frequency-domain. In general, an arbitrary binary sequence can be defined as $a_j=[a_1, a_2, \ldots, a_N]$. In the special case where the temporal length of each code element equals the period of the carrier ($T_o$), the binary coded envelope can be modeled as a series of rectangular pulses of width $T_o$ and height $a_j$ shifted in the time axis by $(j-0.5) T_o$. Therefore, starting with the Fourier transform of a pulse, the analytical spectrum of the binary coded envelope can be obtained using the time-frequency shifting property of the Fourier transform:

$$\mathcal{F}\{E(t)\} = E(\omega) = \frac{\sqrt{2\pi}}{\omega_o} Sinc\left(\frac{\omega}{\omega_o}\right)\sum_{j=1}^{N} a_j \exp[i\omega T_o(j-0.5)] \quad (5)$$

where $\omega_o$ and i are the carrier angular frequency and the imaginary unit, respectively. Finally, the analytical spectrum of the binary phase coded signal can be calculated through the convolution of equation (5) and the spectrum of the carrier waveform:

$$\mathcal{F}\{f(t)\} = \quad (6)$$

$$F(\omega) = \frac{\pi}{i\omega_o}\sum_{j=1}^{N}\left[a_j Sinc\left(\frac{\omega-\omega_o}{\omega_o}\right)\exp[-iT_o(j-0.5)(\omega-\omega_o)] - a_j Sinc\left(\frac{\omega+\omega_o}{\omega_o}\right)\exp[-iT_o(j-0.5)(\omega+\omega_o)]\right]$$

Equation (6) suggests that the spectrum of the binary coded signal consists of a series of weighted "sinc" functions yielding a narrow-band waveform with most of its energy located at the carrier frequency (narrow-band signal).

The thermophotonic response (Planck radiation emission) of a non-opaque turbid medium to a binary phase code excitation can be obtained through coupling of the optical and thermal-wave fields, where the total optical field (coherent+scattered) is the source of thermal-wave generation. As a simple example, the response of black body absorbers in a turbid medium is investigated. That is, the binary phase code excitation is applied to the surface (z=0) of a turbid medium with known scattering and absorption coefficients ($\mu_s$ and $\mu_a$, respectively), where, after interaction with the turbid medium, the attenuated light is completely absorbed at z=l and thermal waves are generated. The energy fluence, I(z), of the one-dimensional, uniform, collimated beam normally incident on a homogeneous scattering and absorbing medium has been calculated by Prahl et al.[7]. Using this approximation, the thermal-wave problem can be formulated by adding a depth dependent source term to the heat diffusion differential equation (due to absorption by the medium) as well as an attenuated heat source at z=l through a boundary condition:

$$\begin{cases} \frac{\partial^2 \theta(z;\omega)}{\partial z^2} - \sigma^2 \theta(z;\omega) = -\frac{\mu_a}{k} I(z) F(\omega) & (7) \\ -k\frac{\partial \theta(z;\omega)}{\partial z}\bigg|_{z=0} = 0 & (I) \\ -k\frac{\partial \theta(z;\omega)}{\partial z}\bigg|_{z=l} = I(l) F(\omega) & (II) \\ \theta(z;\omega) = \mathcal{F}\{T(z,t) - T_\infty\} \end{cases}$$

where k, $\alpha$, and $F(\omega)$ are thermal conductivity, thermal diffusivity and the spectrum of the applied binary phase code excitation, respectively, and $\sigma=\sqrt{i\omega/\alpha}$ is the complex wavenumber. Solving the frequency-domain differential equation subject to the boundary conditions and considering an average value for the infrared absorption coefficient within the spectral range of the detector ($\bar{\mu}_{IR}$), the conductive heat transfer spectrum of the thermophotonic signal can be calculated as:

$$S_c(l;\omega) \propto \bar{\mu}_{IR} \int_0^l \theta(z;\omega)\exp(-\bar{\mu}_{IR}z)\,dz = \quad (8)$$

$$\bar{\mu}_{IR}\left[\frac{A}{\sigma-\bar{\mu}_{IR}}(\exp[(\sigma-\bar{\mu}_{IR})l]-1) - \frac{B}{\sigma+\bar{\mu}_{IR}}(\exp[-(\sigma+\bar{\mu}_{IR})l]-1) - \frac{C}{\mu_{eff}+\bar{\mu}_{IR}}(\exp[-(\mu_{eff}+\bar{\mu}_{IR})l]-1) - \frac{D}{\mu_t+\bar{\mu}_{IR}}(\exp[-(\mu_t+\bar{\mu}_{IR})l]-1)\right]$$

However, the infrared emission captured by the detector is the superposition of (8) and the direct Planck emission from the black-body absorber, attenuated through the turbid medium (9).

$$S(l;\omega) \propto S_c(l;\omega) + \theta(l;\omega)\exp(-\bar{\mu}_{IR}l) \quad (9)$$

Equations (6) and (9) formulate the spectra of the applied binary phase coded excitation (i.e. the matched/mismatched filter) and the thermophotonic response of a subsurface absorber at depth l to such excitation, respectively. Consequently, one can calculate the matched-filter cross-correlation signal and its phase analytically as (3) and (4), respectively, or experimentally via the algorithm depicted in FIG. 3(b).

FIGS. 4(b) and 4(c) plot theoretical comparisons of the CC signals obtained from chirp (dashed lines) and binary phase coded (solid lines) modulation techniques. Optical and thermal properties of dental enamel were used as the properties of the turbid medium. The CC responses clearly show that binary phase code modulation significantly improves the axial resolution (FWHM of the main peaks) as well as the SNR. Moreover, the plots suggest that matched/mismatched filtering using phase modulation can exhibit energy localization normally encountered in propagating hyperbolic wave-fields. As a result, one can obtain localized information from absorbers at different depths by investigating the CC plots at the corresponding delay times or alternatively obtain iso-delay (iso-depth) images in a thermophotonic radar imaging system. Consequently, by scanning the image plane in the delay time axis one can obtain thermal coherence tomographic images and locally resolve absorbers in a diffuse field.

In another example embodiment, the aforementioned systems and methods are employed for the detection and/or monitoring of teeth. Teeth (including enamel, dentin, root and or cementum) are an optically turbid medium, therefore when light enters the tooth it scatters and gets absorbed along its path. Optical extinction depth is defined as the effective depth within which the light can get absorbed and generates heat, including both absorption and scattering effects. Interpolating the enamel extinction coefficient from the IR spectrum of dental enamel reported by Jones and Fried, the optical extinction depth is roughly 250 µm for the 808-nm laser light. However, as photon absorption events are responsible for generating thermal signals, it is the optical absorption depth (~1 cm) that is the controlling factor, or, more precisely, a superposition of 1) a conduction heat transfer mode whose depth is controlled by the thermal-wave centroid determined by the optical extinction depth and thermal diffusion length; and 2) a radiation heat transfer mode whose depth is controlled by the optical extinction depth: When modulated optical excitation is absorbed inside the tooth, the subsequent heat generation gives two contributions to the infrared camera signal. First, an oscillatory heat distribution (thermal-wave) is formed at or near the surface within a thermal diffusion length (at the modulation frequency of the absorbed optical excitation) which will conductively reach the surface of the tooth and contribute to the camera signal in the form of a depth integral through infrared emission.

Second, direct thermal infrared (Planck) emission occurs from all absorption locations (surface and subsurface) with IR photon back-propagation through the enamel due to the 15 to 20% transmittance of enamel in the mid-infrared region. Considering the speed of light and the thickness of enamel, the latter contribution is instantaneous and therefore there will be no phase shift between the direct infrared (Planck) emission responses received from different depths in the tooth. Consequently, it is believed that there will be no contrast contribution from this type of direct emission in the thermophotonic lock-in phase image; however, direct emission will contribute to the amplitude image contrast as these images are concerned with the amplitude of infrared emission (number of IR photons) received at a specific modulation frequency, a function of the local absorption coefficient and optical-to-thermal energy conversion efficiency.

On the other hand, the thermal-wave contribution to the infrared camera signal is not instantaneous as speed of propagation of heat is significantly smaller than that of light. As a result, absorption at different depths will result in different phase values at a fixed modulation frequency. Unlike pure thermal waves generated in opaque media, optically non-saturated photothermal waves carry optical as well as thermal information. The most important feature of thermal waves is that their effective penetration depth can be controlled through the modulation frequency:

$$\mu_{th}(f) = \sqrt{\alpha/\pi f} \tag{10a}$$

and the signal carries optical absorption information from depths $d \leq \mu_{th}(f)$. When the optical extinction depth, $\mu_{ex}(\lambda)$ contribution to the thermal-wave distribution is taken into account, where $\lambda$ is the wavelength of the optical excitation source, in the concept of the thermophotonic-wave centroid, $L(\omega,\lambda)$:

$$L^{-1}(\omega,\lambda) = \mu^{-1}_{th}(\omega) + \mu^{-1}_{ex}(\lambda) \tag{10b}$$

Equation 10(b) comprises the physical principle on which thermophotonic lock-in imaging hinges. In equation 10(b), $\mu_{th}$, $\mu_{ex}$, $\alpha$, and f are thermal diffusion length, optical extinction depth, thermal diffusivity, and modulation frequency, respectively.

Therefore, as photothermal-wave generated infrared emission is the dominant source of contrast in thermophotonic lock-in phase images, one can control the imaging depth by adjusting the modulation frequency according to equation 10. Due to the small thermal diffusivity, $\alpha$, of enamel, dentin and root cementum, the maximum thermal diffusion length (i.e. at modulation frequency ~1 Hz) is on the order of ~300 µm. Therefore, phase images are best used for detecting inhomogeneities at short subsurface distances within the enamel such as the early demineralization and carious lesions while amplitude images can be used to detect deep features due to the large optical absorption depth of enamel. Moreover, biofilm, surface stains and dental plaque which are expected, in principle, to produce contrast in the thermophotonic lock-in images, they will do so minimally and only in the image amplitude due to their transparency to 808 nm NIR excitation source used in this study. The thermophotonic lock-in phase image is physically immune to thin surface absorbers as it is independent of the optical properties of the surface.

The same situation holds for thermal wave radar/thermophotonic radar and binary phase code imaging as well. That is, the cross-correlation amplitude images obtain contributions from both the conductive and direct emission sources while the cross-correlation peak delay time and phase images only receive contribution from the conductive part.

The preceding theoretical arguments related to mechanisms of photothermal generation in teeth and other non-opaque turbid matter are not intended to limit the scope of the embodiments disclosed herein. Moreover, although the above embodiments have been focusing on teeth, it is to be understood that the sample may be any suitable sample that is capable of generating detectable photothermal radiation. For example, sample 130 may be processed or finished material, where the methods described herein are employed for non-destructive testing purposes, especially those that benefit from the characterization of subsurface absorption. These include, but are not confined to, subsurface cracks and defects in metals and coatings; automotive component inspection and quality assurance, including unsintered parts in the green state; aerospace component inspection such as gears and hardened steels, and the determination of the hardness case depth; optical and laser materials and coatings with visually imperceptible blemishes; coatings and alloys, biomedical materials and soft and hard tissue diagnostics, cracks and defects in dental restorations including direct placed and indirect fabricated prosthetics, defects or ill-fitting prosthetics linked to dental implants, defects at the margins or junctions of tooth and dental restorations, and all other materials applications to which photothermal diagnostics has been and can be applied[11]. In dental applications, cracks and defects in dental restorations including direct placed and indirect fabricated prosthetics, defects or ill-fitting prosthetics linked to dental implants, defects at the margins or junctions of tooth and dental restorations.

Additional applications of the preceding embodiments to the detection of defects in dental materials includes the following: detecting and monitoring the effect of various agents, treatments and therapies on in-vivo or in-vitro teeth or samples to determine whether or not they create lesions or erosions, stabilize these areas of tissue loss or promote regeneration of lost tissue; detecting and monitoring changes in tooth structure as additional evidence of various disease process such as bruxism, gastro-esophagel reflux, Tempro-Mandibular Joint Dysfunction, and the like; detecting, examining and scanning a tooth surface whether intact or prepared for the placement of a direct or indirect restoration to ensure that the surface is clean, free of defects including cracks or accumulations of debris, cements, plaque etc. before placement of the restoration; detecting and monitoring defects and or dental caries around the edges of direct placed (amalgam, composite resin and other) dental materials; detecting and monitoring the integrity of dental materials including detection of cracks, craze lines etc. on both direct placed and indirect fabricated dental prosthetics; detecting and monitoring defects at the margins of dental sealants and caries beneath these dental sealants which are placed in the tooth; detecting and monitoring defects and or dental caries at the margins of indirectly placed dental restorations including full crowns, inlays, onlays, bridges etc. made of gold, composite and or porcelain or other dental materials; detecting, monitoring and confirming the fit and marginal integrity of direct and indirect placed dental materials into prepared tooth surfaces; detecting and monitoring the fit of precision attached dental restorations to ensure that the attachments are completely seated; detecting and monitoring the fit of mesostructures onto osseous integrated dental implants on initial placement and over the lifetime of the prosthesis; detecting and monitoring the integrity of materials used in the manufacture of dental prosthesis including osseous integrated implants, mesostructures and or superstructures, frameworks of fixed and removable prosthesis made of metal alloy, sintered porcelain and other materials; detecting and monitoring carious lesions and or defects around orthodontic brackets and other materials that are bonded on to the tooth surface not excluding bonded bridgework, veneers and retainers or other surface sealants; detecting the pulp chamber and or root canal system inside the tooth surface while performing endodontic therapy; confirming the marginal integrity of the endodontic obturation or filling of the root canal system of a tooth; detecting cracks both on the outside of the tooth surface and from within a cavity preparation or within the confines of the pulp chamber or root canal system; detecting and examining the anatomical structure of root apices while performing surgery in this area; detecting, examining and locating neurovascular bundle while performing surgery in the maxilla and or mandible; detecting and monitoring the recession or movement or migration of the gingival tissue from the CEJ; detecting and monitoring the evolution of erosion lesions or lesions due to the exposure of acids on the tooth surface or surface of the dental restorative materials; detecting and monitoring the evolution of carious lesions or erosion lesions and how various therapies can enhance, stabilize or reduce lesions size; and incorporating this into a preventive based program that can be used in a clinical practice or a public health programme; combining the images, information into a data base that is patient specific, specific for a particular dental practice, for a particular age group, particular group of teeth, particular sex or ethnic group or particular postal code or geographic region to provide information on the health and status of the teeth, prosthesis or other entities studied; taking the combined images and information from this data base to provide historical information and or epidemiologic information on the caries present, size of lesion, state of dental materials in various environments, and other information on the oral health and integrity of the dental materials and prosthetics; taking the combined images and information from this data base on a patient specific, gender specific or other groupings and comparing it against known risk factors for caries, erosion, bruxism and other oral disorders and conditions to develop a risk profile or risk ranking for a patient or a population group; using the information in this data base to provide guidance on the various therapies, pathologic situations to patients, oral health providers, providers of the various dental programs and manufacturers of the various therapies; and detecting and monitoring the integrity of various dental instruments including but not limited to dental burs, diamond dental burs, surgical elevators, endodontic files and instruments and or dental scalers and or curettes to ensure that there are no defects that would affect the integrity of the material or instrument while it is being used during a procedure.

The following examples are presented to enable those skilled in the art to understand and to practice embodiments of the present disclosure. They should not be considered as a limitation on the scope of the present embodiments, but merely as being illustrative and representative thereof.

EXAMPLES

Example 1

Early Detection of Dental Caries

In order to apply controlled demineralization to tooth samples, a demineralizing/artificial caries solution was prepared. The solution was an acidified gel, consisting of 0.1M lactic acid gelled to a thick consistency with 6% w/v hydroxyethylcellulose and the pH adjusted to 4.5 with 0.1M NaOH. Demineralization with acidified gel approximates the natural carious lesion as it mimics the properties of actual dental plaques in the oral cavity. Previous studies show that this solution can produce a subsurface lesion in enamel with a sound surface layer which is characteristic of an early carious lesion[1].

As it was desired to observe the contrast between demineralized and healthy areas in a whole tooth, a treatment protocol was followed in which the interrogated surface of the sample was covered with two coatings of commercial transparent nail polish except for a rectangular or square window, henceforth referred to as the treatment window. The demineralization on the window was carried out by submerging the sample upside down in a polypropylene test tube containing 30 ml of demineralizing/artificial caries solution. After the treatment period the sample was removed from the gel, rinsed under running tap water for approximately 1 minute and dried in air for 5 minutes. Then, the transparent nail polish was removed from the interrogated surface with acetone and the sample was again rinsed, dried, and stored in the air-tight humid box for at least 24 hours before the imaging. For consecutive demineralization, after the imaging step the sample was again covered with the transparent nail polish (except for the treatment window) and treated/demineralized for additional days in order to investigate the progression of demineralization and evolution of the artificial carious lesion with time.

FIG. 5(a) shows an optical image of sample A1 before application of demineralization in the treatment window. The dashed rectangle in this figure shows the area that was imaged using the thermophotonic lock-in system while the solid rectangle depicts the location of the treatment window. The optical image shows traces of a discontinuity on the surface of enamel (feature 1). The two vertical lines on the root area show the approximate lateral position of the treatment window (solid rectangle). These lines were meant to aid the operator with sample alignment and are of no scientific importance. FIG. 5(b) "F" shows the dental radiograph of the untreated sample ("before") at the same view as the optical image and FIG. 5(b) "S" shows the side view indicated by the arrow in the optical image (FIG. 5(a)). Based on these radiographs and visual examination sample A1 was a healthy tooth before application of artificial caries treatment and it is interesting to see that the discontinuity or crack on the enamel surface (feature 1) could not be resolved in either of the dental radiographs.

Figure 5:
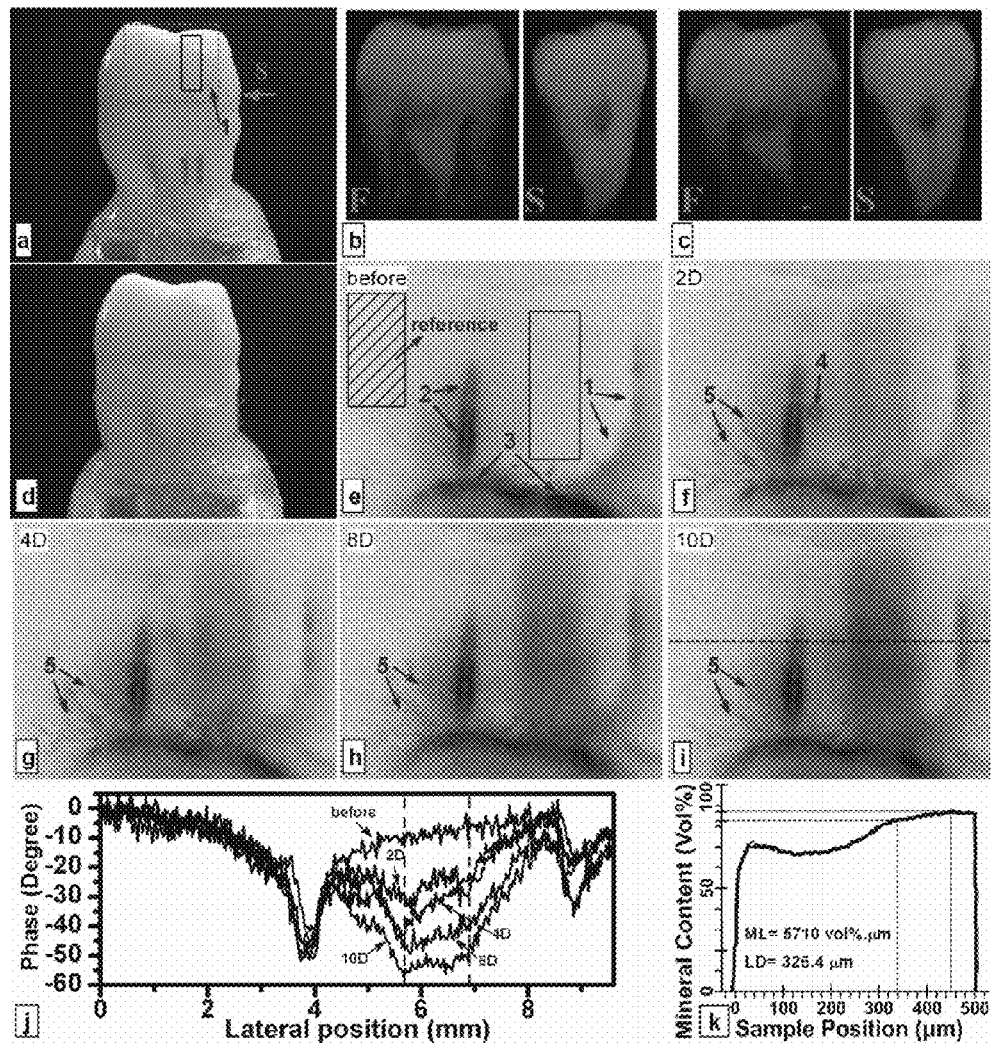
FIG. 5 shows (a) an optical image, (b) front (F) and side (S) dental radiographs of sample A1 (human bicuspid tooth) before treatment; and (c) front (F) and side (S) dental radiographs (d) optical image of sample A1 after 10 days of demineralization treatment with an artificial caries solution within the treatment window; thermophotonic lock-in phase images of sample A1 (e) before treatment and after (f) 2, (g) 4, (h) 8, and (i) 10 days of demineralization with an artificial caries solution within the treatment window; (j) phase profiles along the dashed line shown in FIG. 5i for samples at several demineralization stages (dashed vertical lines show the location of the treatment window); and (k) Transverse micro-radiographic mineral profile along the center of the treatment window of the 10-day demineralized sample.

FIGS. 5(b-c) and 5(d) are the x-ray radiographs and the optical image, respectively, taken from sample A1 after 10 days of treatment. None of these images can show even a trace of mineral loss in the treatment window, showing the insensitivity of conventional clinical diagnostic methods to early demineralization or carious lesion formation. FIG. 5(e) depicts the thermophotonic lock-in phase image of sample A1 taken at 10 Hz before application of any treatment. This image not only shows the enamel discontinuity observed in the optical image (feature 1) but also reveals the presence of a vertical crack (feature 2) and the cementoenamel junction (CEJ, feature 3). Neither the x-ray radiographs (FIG. 5(b)) nor the optical image (FIG. 5(a)), could resolve this vertical crack (feature 2). The reason of the high sensitivity of thermophotonic images to cracks is the fissured nature of cracks which enhances the photothermal temperature field through thermal-wave flux localization generating high contrast.

The appearance of the enamel discontinuity in the phase image (feature 1 in FIG. 5(e)) has similar physical origin to that of cracks. It was postulated that feature 1 was caused by the forces applied during the tooth extraction. The appearance of a dark band in the phase images of FIG. 5 (feature 3) at the CEJ level suggests the presence of a border between enamel and cementum, remnants of periodontal ligament at this position. According to the dental literature, enamel of the cervical margin of the tooth is one of the locations which favors plaque formation and is therefore prone to demineralization. It can be seen that all the thermophotonic phase images of FIG. 5 can detect feature 3 (the CEJ) with high sensitivity (contrast). In fact, one of the most important advantages of thermophotonic lock-in imaging compared to single point photothermal radiometric (PTR) measurements is the significant improvement in the wealth of data resulting in excellent contrast and reliability of the results in real time and in direct comparison with conventional dental radiographs. Point-by-point measurements would require much longer time spans to produce surface images, which would be impractical in clinical applications.

FIGS. 5(f) to 5(i) show the phase images taken at 2, 4, 8, and 10 days of treatment (mineral loss only within the treatment window), respectively. It should be noted that the same contrast mapping (linear, with identical thresholds) has been used in all thermophotonic lock-in images of FIG. 5 to ensure the validity of comparison between the images. It can be observed that as treatment time increases the treated window becomes more apparent while the other features in the images remain more or less the same. The mean phase values within the treatment window (empty rectangle in FIG. 1(e)) for the untreated, 2D, 4D, 8D, and 10D samples are found to be −7.47°, −25.22°, −31.75°, −42.07°, and −49.66°, respectively. This monotonic decrease in the phase lag is due to the progression of the lesion into the enamel. As the lesion thickness increases, the thermal-wave centroid shifts closer to the surface, thereby decreasing the phase lag between the applied optical excitation and the received infrared response. The phase lag decreases also with respect to the intact state ("before").

Feature 4 in FIG. 5(f) is most probably a material inhomogeneity formed as a result of incomplete removal of nail polish from the enamel surface after the second day of demineralization. The feature disappeared after the next demineralization cycle. It appears that feature 5 is stress-induced cracks that were formed during tooth extraction. The cracks become more apparent toward the later stages of demineralization (FIGS. 5(e) to 5(i)) due to successive nail polish penetration into them. It has been known that nail polish can penetrate tens of micrometers into dental enamel.

FIG. 5(j) is a plot of transverse profiles of the phase images along the dashed line shown in FIG. 5(i). The dashed vertical lines represent the location of the treatment window (centered at 6.27 mm). It can be seen that as demineralization progresses, the absolute thermophotonic phase values increase within the treatment window but remain approximately the same outside the treatment window. Furthermore, examination of these phase profiles reveals that the demineralization and artificial lesion has not only propagated vertically into the enamel but has also spread out laterally. However, the extent of the lesion is always maximal within the treatment window and decreases rapidly laterally away from the treatment window. The two dips in the phase values at ~3.9 mm and ~8.8 mm lateral positions are related to the vertical defects at those locations (features 2 and 1, respectively).

FIG. 5(k) represents the transverse micro-radiographic mineral profile vertically along the center of the treatment window. Mean lesion depth of 326.4 μm and mineral loss of 5,710 vol % μm was reported by the transverse micro-radiographic software for the lesion produced at the center of the treatment window. It can be seen that the lesion retains a relatively well-preserved surface layer with a moderate mineral loss over a large depth. It is somewhat surprising to find such a deep lesion formed after only 10 days of treatment with the artificial caries gel, but it is a well-known fact that the rate of demineralization can vary greatly among teeth[1].

Figure 6:
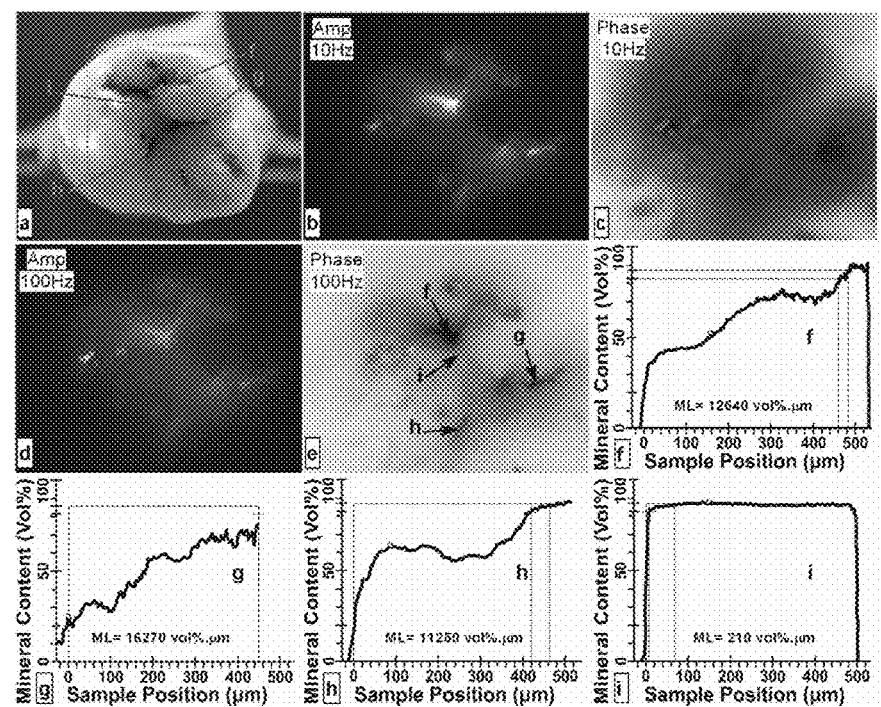
FIG. 6 shows (a) an optical image of sample A2, the occlusal surface of a maxillary molar with stained pits and fissures; thermophotonic (b) amplitude and (c) phase images of sample A2 obtained at 10 Hz; thermophotonic (d) amplitude and (e) phase images of sample A2 obtained at 100 Hz; and (f)-(i) transverse micro-radiographic mineral profiles of points f-i, respectively, as indicated in (e).

FIG. 6 presents the results obtained from sample A2. Unlike Sample A1, the occlusal surface was investigated for this sample. FIG. 6(b) shows the thermophotonic lock-in amplitude image taken at 10 Hz. The amplitude image shows the presence of caries at several locations but the image is rather diffuse. Using this image, four regions of interest (i, f, g, and h) were identified within the imaged area of the optical image (FIG. 6(a)). The thermophotonic lock-in phase image taken at 10 Hz is shown in FIG. 6(c). No feature can be resolved in the blurry phase image. The reason for such poor resolution is the relatively long, diffusion-limited thermal wavelength at 10 Hz. In fact, in these images the contributions from deeper features have resulted in nuisance interferences superposed on features closer to the surface.

Consequently, to avoid the interfering effects of deep features, it was decided to reduce the thermal wavelength by generating the images at 100 Hz in order to be able to effectively detect the areas of mineral loss in the pits and fissures of the occlusal surface and the near-subsurface regions. The resolution improvement at higher frequencies is a well-known behavior of thermal-waves[3] and is clearly visible in the amplitude and phase images obtained at 100 Hz (FIGS. 6(d) and 6(e)). The pits labeled f, g, and h in FIG. 6(e) are shown as carious spots, whereas the groove labelled i is shown as a healthy bright spot (similar to intact regions in images 5b to 5f). Transverse micro-radiographic profiles are shown in FIGS. 6i-f of the dark carious regions f, g, and h and of the groove i, clearly show the presence of mineral losses at points f, g and h while no significant mineral loss can be observed in the mineral profile obtained at i. The transverse micro-radiographic profiles fully validate the results of the non-contacting, non-destructive imaging method.

Example 2a

Non-Destructive Testing of Engineering Materials With Subsurface Absorbers and Early Detection of Dental Caries Using Thermophotonic Radar Imaging The physical principles of light absorption/scattering and thermal-wave generation are the same for the various imaging modalities disclosed herein. The difference lies in the applied optical excitation pattern and the subsequent signal processing algorithm. As discussed above, in thermal wave radar (or thermophotonic radar) imaging a chirp excitation is used instead of a single frequency modulation. As a result, according to equation 5a, the thermal diffusion length is not fixed and the generated thermal-waves dynamically scan a series of depths. One of the problems encountered in thermophotonic lock-in imaging is the compromise one needs to make between the maximum detection depth and the depth resolution. While the low frequency thermal-waves can see deep into the sample, they lack the desired depth resolution; the high frequency thermal-waves, on the other hand, have the exact opposite situation due to the reduced thermal diffusion length.

In order to experimentally investigate the capabilities of the thermophotonic radar method, three samples of engineering and biological materials were designed and prepared. The first sample, B1 400 (FIG. 7(a)), is a black plastic step-wedge sample (step height=200 μm) placed inside a scattering medium (polyvinyl chloride-plastisol (PVCP) with added Titanium dioxide ($TiO_2$) powder for scattering[6]) such that the first step is located approximately 1 mm below the phantom surface. The second sample, B2 420 (FIG. 7(b)), was made using 120 μm-thick Fisher Scientific borosilicate microscope cover slips. The glass was covered by commercial green 430 (on the left) and black 440 (on the right) paints with no paint applied to the center part 450 to form a three-strip pattern. Six additional microscope cover slips were put on the painted slip to simulate 2 absorbers with different absorbing coefficients 720 μm below the surface. To show the application of the Thermophotonic Radar imaging in the dental field, the third sample, B3 460, was chosen to be an extracted human tooth that was locally demineralized using the artificial caries acidic gel within two square shape treatment windows 470, as shown in FIG. 7(c). The left and right windows were treated/demineralized for 10 and 20 days, respectively.

Figure 7:
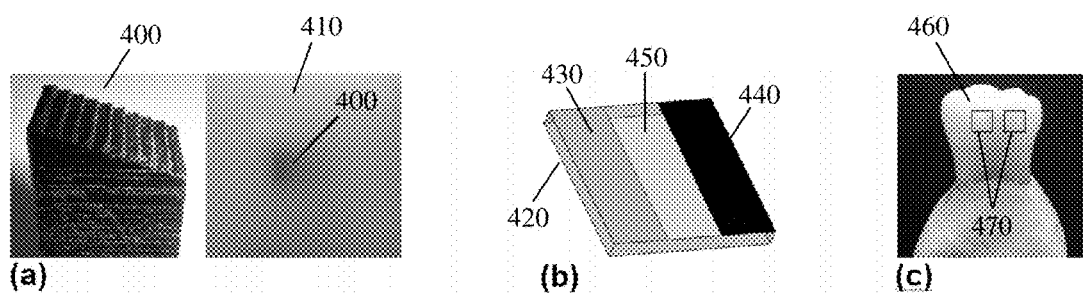
FIG. 7 provides images of (a) sample B1, (left) the plastic step wedge (right) inside the scattering medium, (b) sample B2, strip pattern left to right: green, transparent, black, and (c) sample B3, where the squares in (c) indicate the locations of two demineralization (artificial caries) treatment windows.
Figure 8:
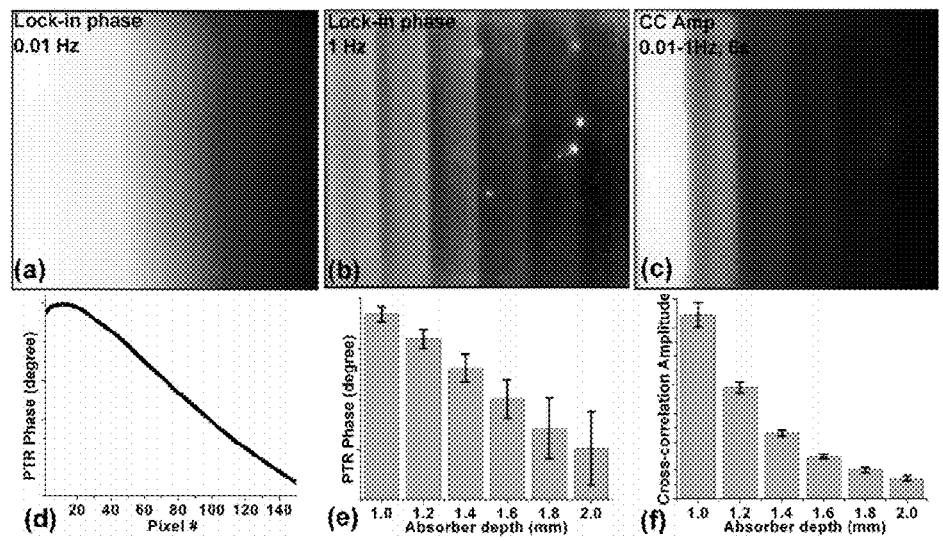
FIG. 8 plots thermal wave radar and phase lock-in (LI) imaging of sample B2, with LI thermography phase images at (a) 0.01 Hz and (b) 1 Hz; (c) Cross-correlation (CC) amplitude image (chirp frequency bandwidth: 0.01-1 Hz in 6 s); (d) mean horizontal LI phase profile of figure (a); and distribution of (e) LI phase and (f) CC amplitude values over the steps.

FIG. 8 shows the results obtained from a comparison study on the depth resolution capabilities of thermophotonic lock-in and thermophotonic radar imaging involving sample B1 (FIG. 7(a)). FIGS. 8(a) and 8(d) show the thermophotonic lock-in phase image obtained at 0.01 Hz and its mean horizontal phase profile, respectively. It can be seen that due to the very large thermal diffusion length at such low modulation frequency it is impossible to resolve the 200-μm-high steps from each other and as a result the phase image appears as a gradient of colors between the two color bar extremes.

FIG. 8(b) shows the thermophotonic lock-in phase image obtained at 1 Hz. The bar plot of FIG. 8(e) depicts the mean phase values on each step along with their standard deviations. The error bars indicate that statistically only the first two steps can be resolved. FIGS. 8(a) and (b) clearly show the maximum detection depth/depth resolution trade-off of thermophotonic lock-in imaging.

FIG. 8(c) is a CC amplitude image obtained from 0.01-1 Hz chirps with duration of 6 s (using the exact same experimental conditions as those used for FIGS. 8(a) and 8(b)) and FIG. 8(f) depicts the mean CC values on each step. It can be seen that the thermophotonic radar imaging not only resolves the steps but also detects them all. These advantages are due to the fact that the matched filtering/cross correlation process puts most energy of the signal under its main narrow peak, improving depth resolution and greatly enhancing the signal to noise ratio, which equals the time (chirp duration)–bandwidth (chirp frequency content) product, thereby improving maximum detection depth.

Figure 9:
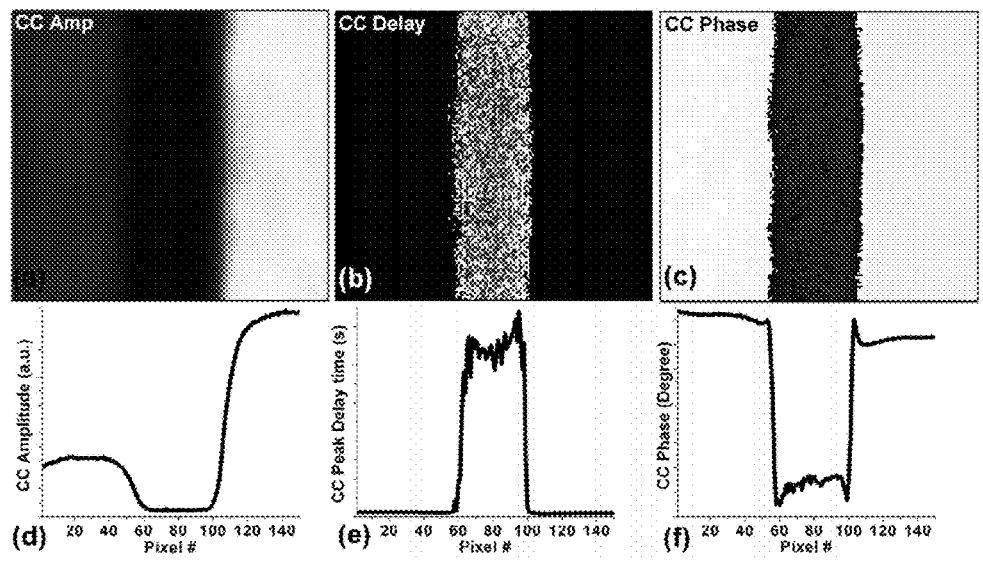
FIG. 9 plots thermal wave radar imaging of sample B2 using (a) CC amplitude, (b) CC peak delay time, (c) CC phase and their mean horizontal profiles (d), (e), and (f), respectively (chirp frequency bandwidth: 0.01-1 Hz in 6 s).

FIG. 9 depicts the results involving sample B2 (FIG. 7(b)) to compare the three contrast parameters that can be used in thermophotonic radar imaging. FIGS. 9(a), 9(b), and 9(c) are the images obtained using cross correlation amplitude, peak delay time, and phase, respectively, and FIGS. 9(d), 9(e), and 9(f) show their horizontal mean profiles. It can be seen that the amplitude channel is truly reflecting the amount of energy absorption by the two equally deep absorbers (green and black paints), yielding significantly different CC amplitude values from them. Consequently, the amplitude channel is not a true measure of the depth of the absorber while the CC peak delay time and phase values are truly linked to the depth of the absorbers as they maintain the same value over the two absorbers regardless of their absorption coefficient (similar to thermophotonic lock-in phase channel). However, in terms of SNR the CC amplitude channel is significantly stronger than peak delay time and phase channels and therefore it may be beneficial to use the amplitude images to complement the information obtained from the phase and peak delay time images.

Figure 10:
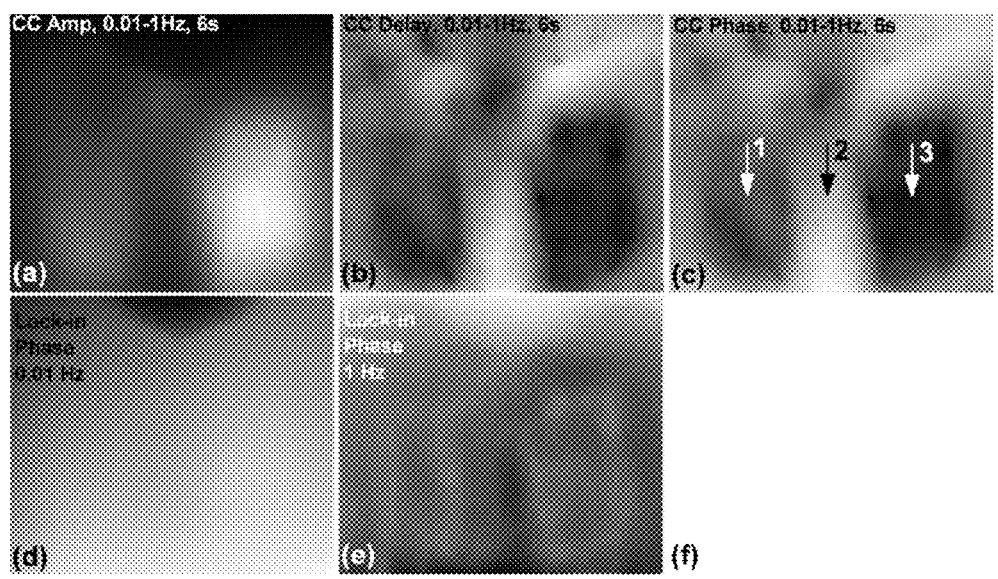
FIG. 10 plots thermal wave radar and thermophotonic lock-in imaging of sample B3, showing (a) CC amplitude image, (b) CC peak delay time image, (c) CC phase image (chirp frequency bandwidth: 0.01-1 Hz in 6 s); thermophotonic lock-in phase images at (d) 0.01 Hz and (e) 1 Hz; and (f) transverse micro-radiographic mineral profiles at points 1-3 indicated in figure (c)

FIGS. 10(a)-(c) show the CC amplitude, peak delay time, and phase images obtained from sample B3. In general, tooth demineralization results in more porosity and leads to more light absorption and scattering that consequently increases the amplitude of thermal-waves and shifts the thermophotonic centroid of Eq. 5b (i.e. phase shift) compared to healthy spots. As a result, the artificially created caries is clearly detectable in all CC images (FIGS. 10(a)-(c)). However, due to the emissivity-normalized nature of peak delay time and phase channels, more details can be resolved in FIGS. 10(b) and (c) compared to FIG. 10(a). The higher contrast of the right treatment window indicates a greater mineral loss due to the additional treatment days. On the other hand, thermophotonic lock-in phase images suffer from low depth resolution at 0.01 Hz (FIG. 10(d)): they cannot probe deep enough at 1 Hz (FIG. 10(e) and cannot show the additional mineral loss in the right treatment window). FIG. 10(f) depicts the transverse micro radiography mineral profiles along points 1-3 depicted in FIG. 10(*c*) and are provided as proof of mineral loss within the treatment windows.

Additional applications to engineered automotive and aerospace materials are in detecting metal hardness case depth and case depth non-uniformities using a thermophotonic radar image of the cross-correlation peak delay times which correspond to case hardness depth[12].

Example 2b

Non-Destructive Testing of Engineering Materials With Subsurface Absorbers and Early Detection of Dental Caries Using Binary Phase Code Imaging Table 1 (shown above) includes the binary phase codes up to 16 bits. These codes are used as an envelope of a single-frequency modulated signal to yield the reference signal for binary phase code imaging.

Figure 11:
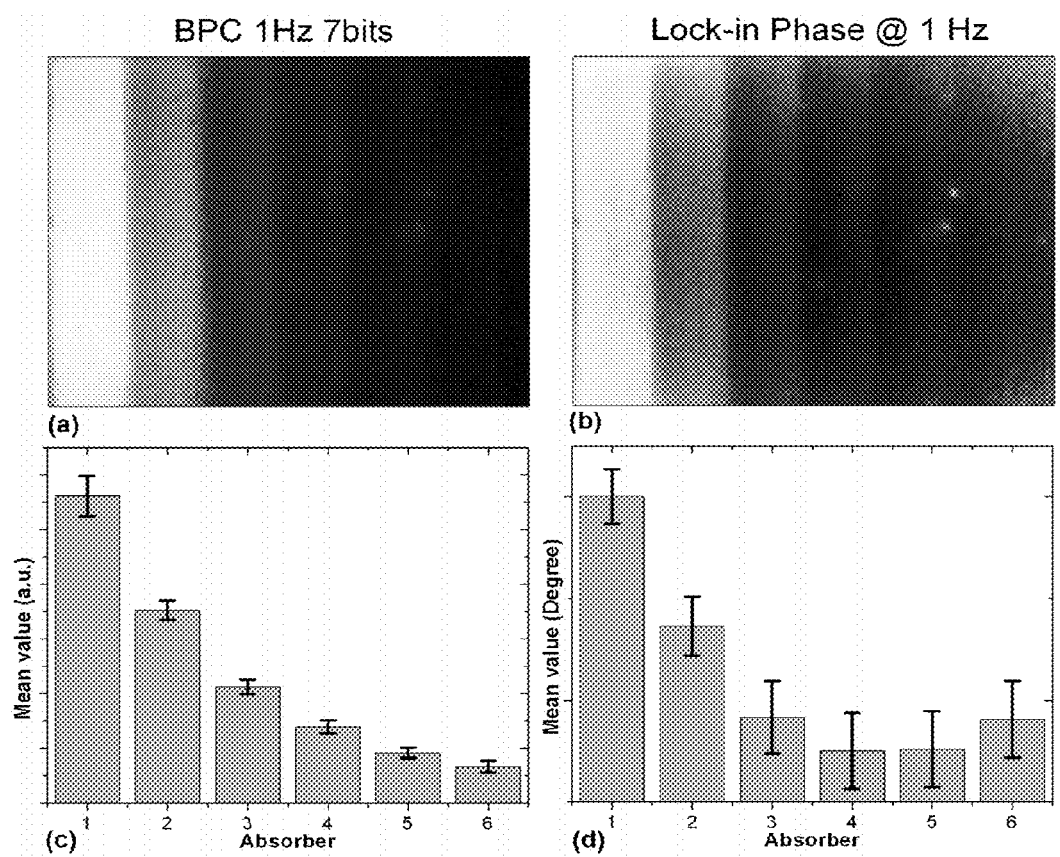
FIG. 11 plots (a) binary phase code and (b) phase LI imaging of sample B1, and distribution of (c) binary phase code image and (d) phase LI image values over the steps of sample B2.

Samples B1 and B3 (FIGS. 7(*a*) and (*c*)) were used to study the capabilities of binary phase code imaging. FIG. 11 shows the results obtained from sample B1 using a 7-bit binary phase coding on a 1 Hz carrier signal (FIGS. 11(*a*) and (*c*)) as well as those of thermophotonic lock-in imaging at 1 Hz (FIGS. 11(*b*) and (*d*)). It can be seen that due to the advantages of matched filtering/cross-correlation the binary phase code image resolves all the steps while the thermophotonic lock-in image can statistically detect only the first two steps. That is, binary phase code imaging has a significantly better depth resolution compared to thermophotonic lock-in imaging.

Figure 12:
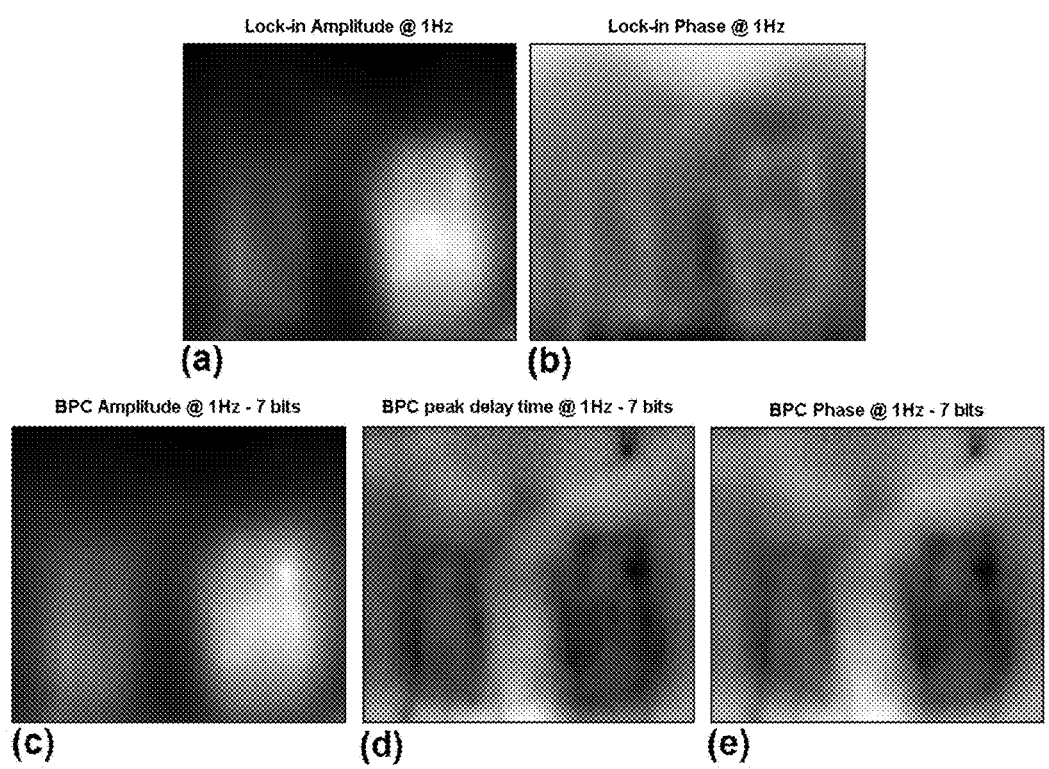
FIG. 12 provides thermophotonic lock-in and binary phase code images of sample B3, with thermophotonic lock-in (a) amplitude and (b) phase images 1 Hz; and binary phase code (c) amplitude image (d) peak delay time image and (e) phase image.

FIG. 12 shows a similar comparison but on an extracted tooth sample (sample B3, FIG. 7(*c*)). While the thermophotonic lock-in amplitude image appears too blurry and the thermophotonic lock-in phase image shows only traces of mineral loss within the treatment windows, the emissivity normalized binary phase code peak delay time and phase images not only detect the regions of mineral loss but also show the additional mineral loss of the right window compared to that of the left window.

FIG. 13 depicts a well-known limitation and challenge of diffusion fields: resolving stacked overlapping defects. FIG. 13(*a*) shows an exploded view of a cross-shaped sample made of two strip absorbers. The deeper strip is a black plastic sample completely absorbing the optical flux, while the shallower strip is a partially absorbing phantom. All other components are transparent polyvinyl chloride-plastisol.

When viewed from the top, the cross sample covers all possible combinations: absorbers at two different depths (the end sections of the absorbing strips, points 1 and 2 in FIG. 13(*b*)) and two absorbers on top of each other (point 3 in FIG. 13(*b*)). FIGS. 13(*b*) and 13(*c*) show the thermophotonic lock-in amplitude and phase images of this sample, respectively. It can be observed that the amplitude image cannot distinguish between the deeper and shallower absorbers (vertical and horizontal strip, respectively). However, the amplitude information can be used to extract and process only those pixels having a high value (i.e. a subsurface absorber). Although the thermophotonic lock-in phase image yields significantly different values over the single absorbers (points 1 and 2) it cannot detect the layered structure of point 3. The axial resolution of both amplitude and phase images is limited by the depth-integrated nature of thermal waves.

FIGS. 13(*d*) and (*e*) are the binary phase code peak delay time images using the temporal data of points 1 and 2 as the matched filter, respectively. When using the temporal camera data of point 1 as the matched filter, all the diffusion waves originating at the same depth as that of point 1 will have their CC peaks located at $\tau=0$ (correlogramic image).

A similar situation arises in FIG. 13(*e*) for diffusion waves from the shallower absorber using the temporal camera data of point 2 as the matched filter. The fact that the layered structure of point 3 shows a maximum correlation to both data of points 1 and 2 ($\tau_p=0$) shows that matched-filter binary phase code imaging can resolve the layered structure axially.

This depth resolved phenomenon is normally a property of propagating hyperbolic wave-fields and not of parabolic (diffusive) fields. The implications of correlogramic imaging can open a new field of generating layer-by-layer subsurface thermal coherence tomography (TCT) using naturally incoherent diffusion waves.

Accordingly, according to some embodiments, correlographic imaging may be employed to produce images at constant delay times. Since each delay time corresponds to a given depth, by making the images at different delay times one can make slice by slice images. The example shown in FIG. 13 provides experimental demonstration that this method provides depth selective (depth slice) images. Although such images may also be produced using chirped waveforms, binary phase coded waveforms generally provide superior axial resolution.

An illustration of the capabilities of this correlographic binary phase code imaging modality applied to turbid media thermophotonics (biological tissue) is its ability to detect early caries in human teeth which conventional clinical diagnostic modalities, like radiographs, cannot detect. Early caries remove mineral from areas very close to the enamel surface and create micro-pores which trap light photons and eventually promote close-to-surface light absorption/thermal-wave generation. As a result, thermal-waves from early caries travel less distance to reach the interrogated surface and yield higher amplitude and smaller phase lag/delay compared to those of intact regions.

Figure 14:
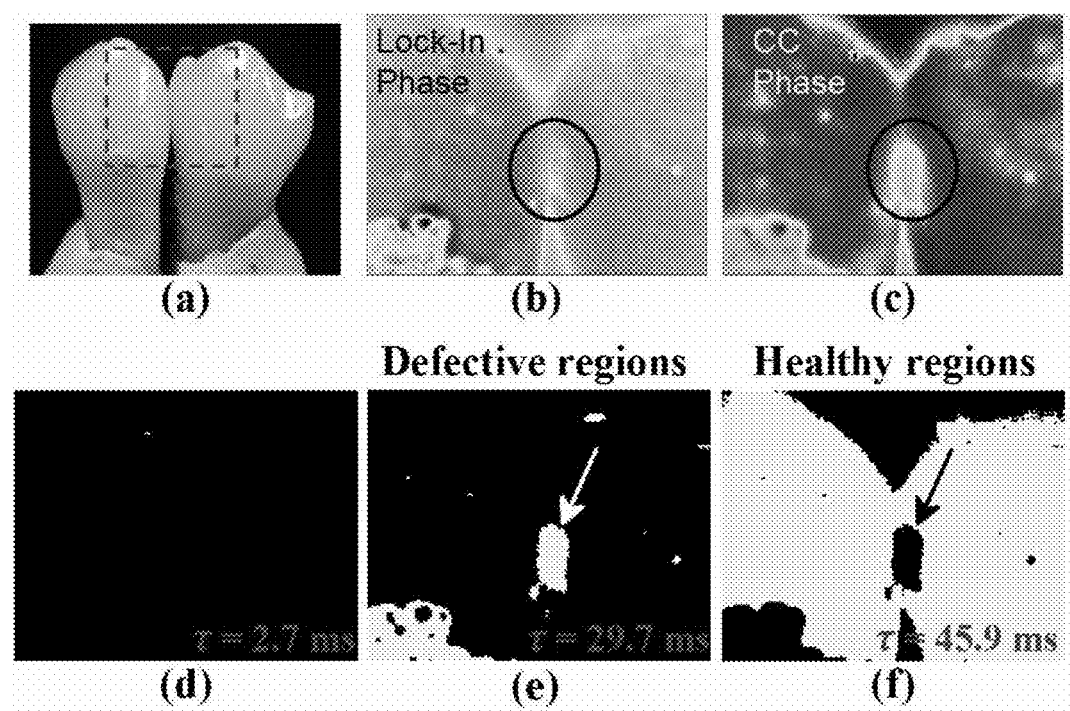
FIG. 14 (a) Teeth matrix with hidden inter-proximal early caries. The rectangle shows the imaged area. (b) Conventional LIT and (c) binary phase code phase images of teeth matrix. (d-f) thermal coherence tomographic images obtained as several delay times differentiating between the defective (e) and healthy (f) regions.

However, an important shortcoming of dental thermophotonic lock-in imaging is its inability to detect interproximal (in between teeth) caries when inspected from the accessible buccal (front) surface. A comparison of thermophotonic lock-in and binary phase code phase images of FIGS. 14(*b*) and 14(*c*) under identical experimental conditions, shows how the enhanced axial resolution of the binary phase code imaging can resolve deep interproximal caries. Moreover, by constructing images (such as amplitude or phase images) at given delay times one can perform depth-selective slicing (thermal coherence tomography) in the turbid medium to resolve the defective regions, FIG. 14(*e*), from the intact areas, FIG. 14(*f*).

Figure 15:
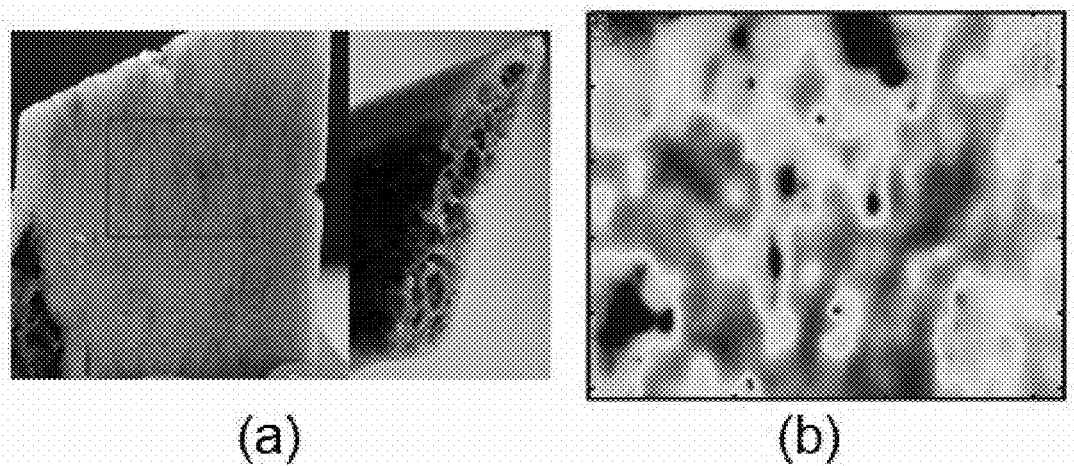
FIG. 15 (a) Optical image of goat bone. The rectangle shows the images area. (b) binary phase code phase images at 1 Hz using a 7 bit binary code.

FIG. 15(*a*) shows the optical image of the interrogated surface of a goat bone along with its cross section. The optical image shows that the spongy trabecular bone is covered by the more dense cortical bone on the surface. FIG. 15(*b*) is the phase image obtained using the binary phase code technique. The low carrier frequency of 1 Hz ensures penetration of thermal-waves into the trabecular structure, while the depth-resolved nature of phase modulated matched filtering reveals the trabecular structure that lies right below the cortical overlayer.

FIG. 15 demonstrates that the depth-selective thermophotonic radar imaging methods disclosed herein are potentially suitable for the imaging of bone structure. Such imaging can be employed to support the identification of bone osteoporosis, and in particular, early bone osteoporosis. Indeed, the present example imaging methods could be employed for screening of osteoporosis. For example, the measured image may be processed according to known image processing techniques to identify abnormal bone condition, such as, by generating, based on the image, a measure of bone health, and comparing the measure to thresholds, normal ranges, or other calibration parameters. It is noted that at present, direct expenditures for treatment of osteoporotic fracture in the U.S. are estimated at $10-$15 billion annually, and that no imaging methodology currently exists for the early diagnosis of osteoporosis.

Additional applications to engineered automotive and aerospace materials are in detecting metal hardness case depth and case depth non-uniformities using a binary phase code image of the cross-correlation peak delay times which correspond to case hardness depth[12].

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1. B. T. Amaechi, S. M. Higham, and W. M. Edgar, "Factors affecting the development of carious lesions in bovine teeth in vitro," *Archs. Oral Biol.* 43, 619-628 (1998).
2. Y. Iijima, O. Takagi, H. Duschner, J. Ruben, and J. Arends, "Influence of nail varnish on the remineralization of enamel single sections assessed by microradiography and confocal laser scanning microscopy," *Caries Res.* 32, 393-400 (1998).
3. R. J. Jeon, A. Mandelis, V. Sanchez, and S. H. Abrams "Nonintrusive, noncontacting frequency-domain photothermal radiometry and luminescence depth profilometry of carious and artificial subsurface lesions in human teeth," *J. Biomed. Opt.* 9(4), 804-819 (2004).
4a. A. Mandelis, "Frequency Modulated (FM) Time Delay Photoacoustic and Photothermal Wave Spectroscopies. Technique, Instrumentation and Detection. Part I: Theoretical", Rev. Sci. Instr. 57 (4), 617-621, April, 1986.
4b. A. Mandelis, L. M. L. Borm and J. Tiessinga, "Frequency Modulated (FM) Time Delay Photoacoustic and Photothermal Wave Spectroscopies. Technique, Instrumentation and Detection. Part II: Mirage Effect Spectrometer Design and Performance", Rev. Sci. Instr. 57 (4), 622-629, April, 1986.
4c. A. Mandelis, L. M. L. Borm and J. Tiessinga, "Frequency Modulated (FM) Time Delay Photoacoustic and Photothermal Wave Spectroscopies. Technique, Instrumentation and Detection. Part III: Mirage Effect Spectrometer, Dynamic Range and Comparison to Pseudo Random Binary Sequence (PRBS) Method", Rev. Sci. Instr. 57 (4), 630-635, April, 1986.
5. R. Mulaveesala, J. S. Vaddi, and P. Singh, "Pulse compression approach to infrared non-destructive characterization", Rev. Sci. Instrum. 79, 094901 (2008).
6. N. Tabatabaei and A. Mandelis, "Thermal-Wave Radar: A novel subsurface imaging modality with extended depth-resolution dynamic range" Rev. Sci. Instrum. 80, 034902 (2009).
7. G. M. Spirou, A. A. Oraevsky, A. I. Vitkin, W. M. Whelan, Phys. Med. Biol. 50, N141 (2005).
8. W. Warta, and M. Langenkamp, Lock-in Thermography: Basics and use for evaluation electronic devices and materials by O. Breitenstein, page 31, second edition, Springer.
9. X. Maldague and S. Marinetti, J. Appl. Phys. 79, 2694 (1996).
10. Rohling H., Plagge W., "Mismatched-filter design for periodical binary phased signals", IEEE Transactions on Aerospace and electric systems, V25, N6, November 1989.
11. A. Mandelis, "Principles and Perspectives on Photothermal and Photoacoustic Phenomena", Elsevier, New York (1992), ISBN 0 444 01641 4; A. Mandelis, "Non-Destructive Evaluation", PTR Prentice Hall, Englewood Cliffs, N. J., (1993), ISBN 0-13-147430-8; Vol. III: "*Life and Earth Sciences*", A. Mandelis and P. Hess, Eds., SPIE Publishing Optical Engineering Press, Bellingham, Wash. February 1997, ISBN 0-8194-2450-1.
12. X. Guo, K. Sivagurunathan, J. Garcia, A. Mandelis, S. Giunta, and S. Milletari, "Laser photothermal radiometric instrumentation for fast in-line measurements of industrial steel hardness inspection and quality control", Appl. Opt. 48 No. 7, C11-C23, 1 Mar. 2009.

Therefore what is claimed is:

1. A method of performing thermophotonic imaging, said method comprising the steps of:
    providing a sample;
    providing an optical source having a wavelength selected to generate photothermal radiation within said sample;
    providing an imaging camera with an optical bandwidth selected for detection of said photothermal radiation;
    generating a reference waveform comprising a plurality of modulation cycles, wherein said reference waveform comprises multiple frequency components;
    producing a modulated optical beam by modulating an intensity of an optical beam emitted by said optical source according to said reference waveform;
    illuminating said sample with said modulated optical beam;
    imaging said photothermal radiation with said imaging camera;
    recording a plurality of averaged image frames at time offsets corresponding to different values of said reference waveform; and
    processing said averaged image frames and said reference waveform to obtain an image relating to said photothermal radiation, wherein said image is a cross-correlation image obtained by calculating a complex cross-correlation of said reference waveform and each pixel of said averaged image frames, thereby obtaining a complex cross-correlation signal for each pixel, and processing the complex cross-correlation signals to obtain the cross-correlation image;
    wherein said cross-correlation image is one of:
        (i) a cross-correlation peak amplitude image obtained by determining, for each said pixel, a peak amplitude value of a peak in a real part of said cross-correlation signal;
        (ii) a cross-correlation peak delay image obtained by determining, for each said pixel, a delay of a peak in a real part of said complex cross-correlation signal; and
        (iii) a cross-correlation phase image obtained by the steps of:
            obtaining a second complex cross-correlation signal of a quadrature waveform and each pixel of said averaged image frames, wherein said quadrature waveform is based on said reference waveform;

forming a complex quantity comprising a real portion of first complex cross-correlation signal and a real portion of said second complex cross-correlation signal; and obtaining said phase image by determining, for each pixel, a phase angle of said complex quantity at a pre-selected time delay.

2. The method according to claim 1 wherein said dynamically averaged image frames are obtained according to the following steps:

recording a plurality of image frames at times corresponding to different values of said reference waveform;

repeating, one or more times, said step of recording said image frames at times corresponding to different values of said reference waveform, and dynamically averaging said recorded image frames for each said different value of said reference waveform, thereby obtaining dynamically averaged image frames.

3. The method according to claim 2 wherein said step of recording said plurality of image frames at different values of said reference waveform comprises recording said plurality of image frames over a single modulation cycle/correlation period.

4. The method according to claim 2 wherein said plurality of image frames at different values of said reference waveform are obtained over more than one modulation cycle.

5. The method according to claim 4 wherein a frame acquisition rate of said imaging camera is less than a modulation frequency of said reference waveform.

6. The method according to claim 2 further comprising the step of recording, for each image frame of said plurality of image frames, a substantially instantaneous value of said reference waveform.

7. The method according to claim 6 further comprising the step of generating a quadrature waveform based on said reference waveform, and recording, for each image frame of said plurality of image frames, a substantially instantaneous value of said quadrature waveform.

8. The method according to claim 1 further comprising the step of generating an integration pulse train comprising a series of pulses, wherein each pulse is generated at a time at which an image frame is acquired by said imaging camera, wherein said step of generating of said reference waveform is triggered according to said integration pulse train.

9. The method according to claim 8 wherein said integration pulse train is generated by said imaging camera.

10. The method according to claim 1 further comprising the step of generating a flag pulse train comprising a series of pulses, wherein each pulse is generated at a commencement of a given modulation cycle/correlation period, and identifying one or both of a beginning and an end of said given modulation cycle/correlation period according to said flag pulse train.

11. The method according to claim 1 wherein a modulation frequency of said reference waveform is greater than approximately 0.01 Hz.

12. The method according to claim 1 wherein said reference waveform comprises a single frequency and wherein said image is obtained by lock-in processing.

13. The method according to claim 12 wherein said step of processing said dynamically averaged image frames and said reference waveform comprises, for each pixel in said image, performing the steps of:

multiplying said dynamically averaged image frames by said reference waveform to obtain in-phase product values; and summing said in-phase product values to obtain an in-phase sum;

generating a quadrature waveform based on said reference waveform;

multiplying said dynamically averaged image frames by said quadrature waveform to obtain phase-shifted product values; and summing said phase-shifted product values to obtain a phase-shifted sum.

14. The method according to claim 13 wherein said image is an amplitude image, and wherein said processing further comprises calculating a magnitude of a complex quantity based on said in-phase sum and said phase-shifted sum.

15. The method according to claim 13 wherein said image is a phase image, and wherein said processing further comprises:

calculating a phase angle of a complex quantity based on said in-phase sum and said phase-shifted sum.

16. The method according to claim 1, wherein said reference waveform comprises a frequency chirp.

17. The method according to claim 1, wherein said reference waveform is a binary phase coded waveform.

18. The method according to claim 1 wherein said sample is selected from the group consisting of automotive components, aerospace components, an optical material, a laser material, a biomedical material, and a biological tissue.

19. The method according to claim 1 wherein said sample is a material comprising one or more of a subsurface crack and a delamination.

20. The method according to claim 1 wherein said sample is an unsintered component in a green state.

21. The method according to claim 1 further comprising the step of determining a case hardness depth.

22. The method according to claim 1 wherein said sample is a dental sample, the method including the step of displaying the image.

23. The method according to claim 1 wherein said sample is a dental or medical instrument.

24. The method according to claim 1 wherein said sample includes bone, wherein the step of imaging the photothermal radiation with the imaging camera includes imaging photothermal radiation generated within the bone.

25. The method according to claim 24 wherein the bone is covered with tissue, and wherein the optical source is configured for transmitting at least a portion of the optical beam through the tissue for the generation of the photothermal radiation within the bone.

26. The method according to claim 24 further wherein a modulation frequency of the modulated optical beam is selected to support penetration of the photothermal radiation within a trabecular structure of the bone.

27. The method according to claim 24 further including the step of identifying an onset or presence of osteoporosis in the bone based on the image.

28. The method according to claim 22 further wherein said dental sample is a tooth sample or whole groups of teeth.

29. The method according to claim 22 wherein the dental sample is a tooth, the method further comprising the step of analyzing said image to determine one or more of a presence and a location of demineralization, erosion or dental caries in said tooth.

30. The method according to claim 22 further comprising the step of monitoring an evolution of one or more of demineralization, erosion and dental caries by comparing said image to one or more other images.

31. The method according to claim 22 wherein the image is a first image, the method further comprising the step of obtaining additional image of the dental sample after a time delay, and comparing the first image to the additional image for monitoring changes in the dental sample.

32. The method according to claim 22 wherein the image is a first image, the method further comprising the step of applying a treatment or therapy to said dental sample, obtaining additional image, and comparing the first image to the additional image to assess an efficacy of the treatment or therapy.

33. The method according to claim 22 wherein the dental sample is a tooth surface that is prepared for prepared for placement of a direct or indirect restoration, the method including the step of confirming, based on the image, suitability of the tooth surface for placement of the restoration.

34. The method according to claim 22 wherein the dental sample includes a tooth having a dental material placed directly thereon, wherein the image includes a region around an edge of the dental material for detecting or monitoring a defect around the edge of the dental material.

35. The method according to claim 34 wherein the dental material is a dental sealant.

36. The method according to claim 22 wherein the dental sample includes a tooth having a dental prosthetic, wherein the image includes the dental prosthetic for detecting or monitoring a defect associated with the dental prosthetic.

37. The method according to claim 22 wherein the dental sample includes a tooth having a dental restoration attached thereto, wherein the image includes the dental restoration for detecting or monitoring the attachment of the dental restoration.

38. The method according to claim 22 wherein the dental sample includes a dental implant, wherein the image includes the dental implant for detecting or monitoring the integrity of the dental implant.

39. The method according to claim 22 wherein the image includes at least one of a pulp chamber and root canal system of the dental sample.

40. The method according to claim 22 wherein the image includes an anatomical structure of root apices or the neurovascular bundle.

41. The method according to claim 1 further comprising the step of identifying a defect region in the image.

42. The method according to claim 41 further comprising the step of displaying the defect region in a color associated with the defect region.

43. The method according to claim 42 wherein the color is associated with a relative size of the defect region.

44. The method according to claim 23 wherein said dental or medical instrument is selected from the group consisting of endodontic instruments, catheters and other indwelling instruments.

45. The method according to claim 1 wherein said wavelength is selected to lie within a range of approximately 600 nm to 2000 nm.

46. The method according to claim 1 wherein said imaging camera is selected to have a spectral response overlapping with at least a portion of the mid-infrared spectrum.

47. A method of performing thermophotonic imaging, said method comprising the steps of:
providing a sample;
providing an optical source having a wavelength selected to generate photothermal radiation within said sample;
providing an imaging camera with an optical bandwidth selected for detection of said photothermal radiation;
generating a reference waveform comprising a binary phase coded waveform having a plurality of modulation cycles, wherein said reference waveform comprises multiple frequency components;
producing a modulated optical beam by modulating an intensity of an optical beam emitted by said optical source according to said reference waveform;
illuminating said sample with said modulated optical beam;
imaging said photothermal radiation with said imaging camera;
recording a plurality of averaged image frames at time offsets corresponding to different values of said reference waveform; and
processing said averaged image frames and said reference waveform to obtain an image relating to said photothermal radiation, wherein said image is a cross-correlation image obtained by calculating a complex cross-correlation of said reference waveform and each pixel of said averaged image frames, thereby obtaining a complex cross-correlation signal for each pixel, and processing the complex cross-correlation signals to obtain the cross-correlation image;
wherein said cross-correlation image is one of:
(i) a cross-correlation peak amplitude image obtained by determining, for each said pixel, a peak amplitude value of a peak in a real part of said cross-correlation signal;
(ii) a cross-correlation peak delay image obtained by determining, for each said pixel, a delay of a peak in a real part of said complex cross-correlation signal; and
(iii) a cross-correlation phase image obtained by the steps of:
obtaining a second complex cross-correlation signal of a quadrature waveform and each pixel of said averaged image frames, wherein said quadrature waveform is based on said reference waveform;
forming a complex quantity comprising a real portion of first complex cross-correlation signal and a real portion of said second complex cross-correlation signal; and
obtaining said phase image by determining, for each pixel, a phase angle of said complex quantity at a pre-selected time delay.

* * * * *